(12) United States Patent
Moras et al.

(10) Patent No.: US 8,198,263 B2
(45) Date of Patent: Jun. 12, 2012

(54) VITAMIN D DERIVATIVES ACTIVE ON THE VITAMIN D NUCLEAR RECEPTOR, PREPARATION AND USES THEREOF

(75) Inventors: Dino Moras, Lampertheim (FR); Antonio Mourino-Mosquera, Ames (ES); Luis Cezar Rodrigues, Santiago De Compostela (ES); Natacha Rochel, Strasbourg (FR); Jean-Marie Wurtz, Drusenheim (FR)

(73) Assignees: Centre National de la Recherche Scientifique, Paris (FR); Universite De Strasbourg, Strasbourg (ES); Universidad De Santiago De Compostela, Santiago de Compostela (ES); Institut National de la Sante Et de la Recherche Medicale, Paris (FR)

( * ) Notice: Subject to any disclaimer, the term of this patent is extended or adjusted under 35 U.S.C. 154(b) by 829 days.

(21) Appl. No.: 12/088,413

(22) PCT Filed: Sep. 26, 2006

(86) PCT No.: PCT/EP2006/066771
§ 371 (c)(1),
(2), (4) Date: Mar. 27, 2008

(87) PCT Pub. No.: WO2007/039526
PCT Pub. Date: Apr. 12, 2007

(65) Prior Publication Data
US 2009/0131378 A1     May 21, 2009

(30) Foreign Application Priority Data
Sep. 28, 2005   (EP) .................................... 05292017

(51) Int. Cl.
*A61K 31/59* (2006.01)
*C07D 307/12* (2006.01)
*C07C 401/00* (2006.01)

(52) U.S. Cl. .......................... 514/167; 552/653; 549/502

(58) Field of Classification Search .................. 514/167; 549/502; 552/653
See application file for complete search history.

(56) References Cited

FOREIGN PATENT DOCUMENTS
WO         98/51678         11/1998

OTHER PUBLICATIONS

Voskoglou-Nomikos et al., Clinica;l Cancer Research, vol. 9, pp. 4227-4239, Sep. 12, 2003.*
Greschik et al, "Structure-Activity Relationship of Nuclear Receptor-Ligand Interactions", Current Topics in Medicinal Chemistry 2003, 3, pp. 1573-1599.
Bouillon et al, "Prospects for Vitamin D receptor Modulators as Candidate Drugs for Cancer and (Auto) immune Diseases", Recent Results in Cancer Research, 2003, vol. 164, pp. 353-356.

(Continued)

*Primary Examiner* — Sabiha Qazi
(74) *Attorney, Agent, or Firm* — Nixon & Vanderhye P.C.

(57) ABSTRACT

The invention relates to vitamin D derivatives and their uses, particularly in the pharmaceutical industry. The invention discloses compounds having different interesting biological properties, including vitamin D nuclear receptor (VDR) agonist activity, as well as therapeutics methods by administering said compounds, in particular for treating cancer, psoriasis, autoimmune diseases, osteodistrophy and osteoporosis. It further relates to pharmaceutical compositions comprising said compounds and methods for preparing the same.

11 Claims, 3 Drawing Sheets

OTHER PUBLICATIONS

Figure 1:
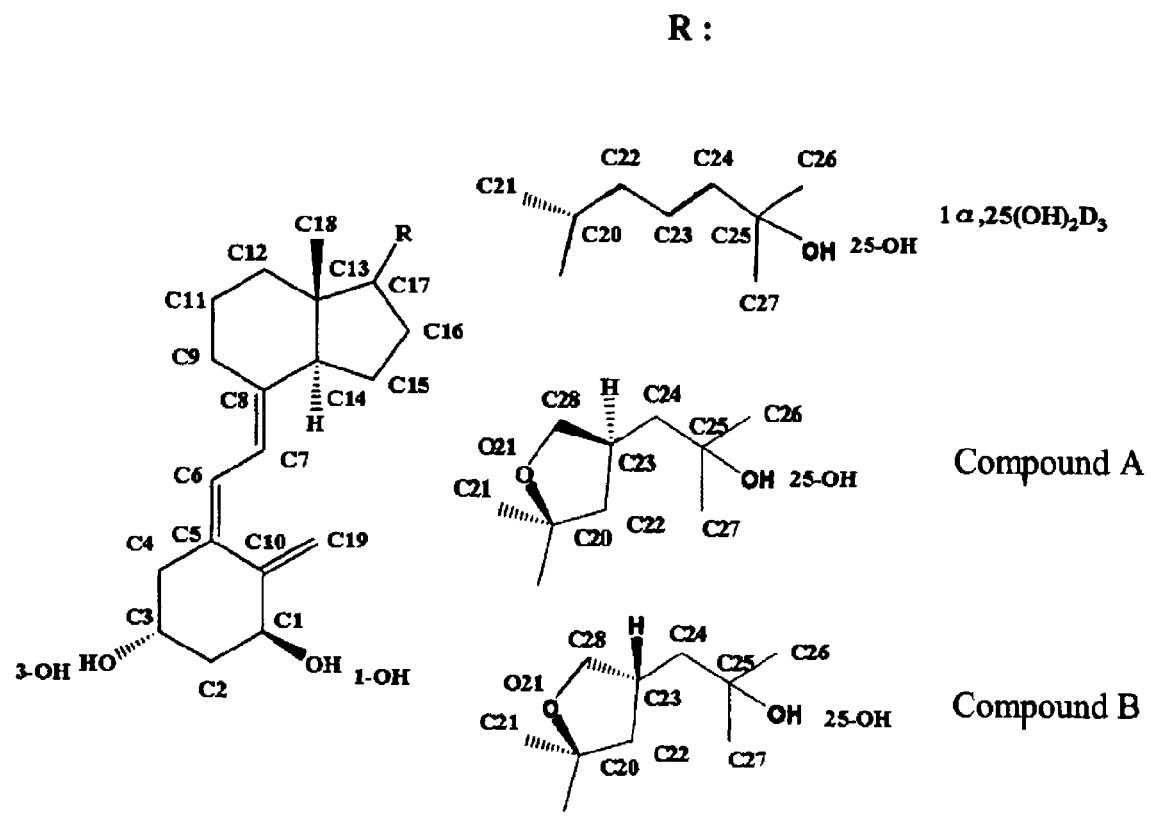

Glass et al, "The coregulator exchange in transcriptional functions of nuclear receptors", (2000) 5 *Genes Dev.* 14, 121-141.

Smith et al, "Coregulator Function: A Key to Understanding Tissue Specificity of Selective Receptor Modulators", (2004) *Endocr. Rev.* 25(1), 45-71.

Norman et al, "Steroid-Hormone Rapid Actions, Membrane Receptors and a Conformational Ensemble Model", (2004) *Nat. Rev. Drug Discov.* 3, 27-41.

DeLuca, "Overview of general physiologic features and functions of vitamin $D^{1-4}$", (2004) *Am. J. Clin. Nutr.* 80 (suppl), 1689S-1696S.

Peleg et al, "Distinct Conformational Changes Induced by 20-epi Analogues of $1\alpha,25$-Dihydroxyvitamin $D_3$ Are Associated with Enhanced Activation of the Vitamin D Receptor", (1995) *J. Biol. Chem.* 270, No. 18, 10551-10558.

Yamamoto et al, "2-Methylene-19-nor-(20S)-1,25-dihydroxyvitamin $D_3$ Potently Stimulates Gene-specific DNA Binding of the Vitamin D Receptor in Osteoblasts", (2003) *J. Biol. Chem.* 278, No. 34, 31756-31765.

Eelen et al, "Superagonistic Action of 14-epi-Analogs of 1,25-Dihydroxyvitamin D Explained by Vitamin D Receptor-Coactivator Interaction", (2005) *Mol. Pharmacol.* vol. 67, No. 5, 1566-1573.

Rochel et al, "The Crystal Structure of the Nuclear Receptor for Vitamin D Bound to Its Natural Ligand", (2000) *Molecular Cell*, vol. 5, 20 173-179.

Tocchini-Valentini et al, "Crystal structures of the vitamin D receptor complexed to superagonist 20-epi ligands", (2001) *Proc Natl Acad Sci USA* 98, No. 10, 5491-5496.

Billas et al, "Structural adaptability in the ligand-binding pocket of the ecdysone hormone receptor", (2003) *Nature* 426, 91-96.

Konno et al, "Synthesis, Biological Evaluation, and Conformational Analysis of A-Ring Diastereomers of 2-Methyl-1,25-dihydroxyvitamin $D_3$ and Their 20-Epimers: Unique Activity Profiles Depending on the Stereochemistry of the A-Ring and at C-20", (2000). *J. Med. Chem.* 43, 4247-4265.

Bouillon et al, "Vitamin D and cancer", The Journal of Steroid Biochemistry & Molecular Biology, 102 (2006) 156-162.

N. Saito, "24,24-Dimethylvitamin $D_3$-26,23-lactones and their $2\alpha$-functionalized analogues as highly potent VDR antagonists," *Tetrahedron* 60: 7954-7961 (2004).

C. Carlberg and A. Mouriño, "New vitamin D receptor ligands," *Expert Opin. Ther. Patents*, 13(6): 761-772 (2003).

* cited by examiner

Fig. 3.1

Fig. 3.2

VITAMIN D DERIVATIVES ACTIVE ON THE VITAMIN D NUCLEAR RECEPTOR, PREPARATION AND USES THEREOF

CROSS-REFERENCE TO RELATED APPLICATIONS

This application is the U.S. National Stage filing of International Application No. PCT/EP2006/066771, filed Sep. 26, 2006, which claims the benefit of European Patent Application No. EP 05292017.0, filed Sep. 28, 2005, the disclosure of which is hereby incorporated by reference.

FIELD OF THE INVENTION

The invention relates to vitamin D derivatives and their uses, particularly in the pharmaceutical industry. The invention discloses compounds having different interesting biological properties, including vitamin D nuclear receptor (VDR) agonist activity, as well as therapeutics methods by administering said compounds, in particular for treating cancer, psoriasis, autoimmune diseases, osteodistrophy and osteoporosis. It further relates to pharmaceutical compositions comprising said compounds and methods for preparing the same.

BACKGROUND OF THE INVENTION

The vitamin D receptor (VDR) is a ligand-dependant transcriptional regulator that belongs to the nuclear receptor (NR) transcription factor family (1), which controls cell growth and differentiation, homeostasis, development, and several physiological processes. Ligand binding to VDR induces a conformational change in the orientation of the AF-2 core motif allowing the interaction with coactivators that mediate the interaction between the nuclear receptor and the basal transcription machinery (2-4).

The plethora of actions of $1\alpha,25(OH)2D_3$, the natural ligand of VDR, in various physiological processes suggested wide clinical applications for vitamin D nuclear VDR ligands in treatments of inflammation (rheumatoid arthritis, psoriatic arthritis), dermatological disorder (psoriasis, photoaging), osteodystrophy, osteoporosis, cancers (breast, prostate, colon, leukemia), and autoimmune diseases (multiple sclerosis, type I diabetes) (5-7). However, the calcemic effects induced by $1\alpha,25(OH)2D_3$ causing hypercalcemia, increasing bone resorption, and soft tissue calcification limit the use of the natural ligand in these clinical applications, and this had led to the development of analogs with reduced side effects.

Some synthetic analogs of $1\alpha,25(OH)_2D_3$ have shown to be superagonists. These analogs are at least 10 times more potent than $1\alpha,25(OH)_2D_3$ in transactivation and present antiproliferative activity several orders of magnitude higher than the $1\alpha,25(OH)_2D_3$ (8-10).

The present invention provides a new class of compounds which are analogs of $1\alpha, 25(OH)_2D_3$. In particular, the invention provides VDR modulators, e.g., agonists or antagonists. Interestingly, the invention also provides superagonists of VDR in vitro test. These analogs are also effective in vivo. It further provides analogs of $1\alpha, 25(OH)2D_3$ which exhibit low-hypercalcemia effect.

SUMMARY OF THE INVENTION

The present invention relates to novel analogs of $1\alpha,25(OH)_2D_3$ presenting an oxolane ring in its aliphatic side chain.

The present invention also relates to a method for preparing novel analogs of $1\alpha,25(OH)_2D_3$.

The present invention also relates to pharmaceutical compositions comprising at least one of the novel $1\alpha, 25(OH)_2D_3$ analogs according to the invention in a pharmaceutically acceptable support, optionally associated with another active agent.

The present invention also relates to the use of compounds according to the invention for the manufacture of a medicament for the treatment of disease states responsive to Vitamin D receptor ligands, including in particular cancer, inflammation, dermatological disorders, autoimmune diseases, osteodystrophy or osteoporosis.

DETAILED DESCRIPTION OF THE INVENTION

An aspect of the invention relates to novel analogs of $1\alpha,25(OH)_2D_3$ presenting the following formula (I):

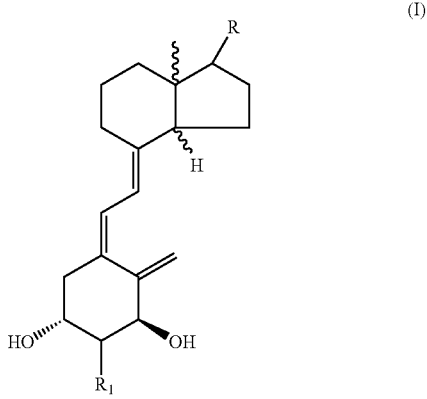

(I)

wherein $R_1$ represents a group selected from a hydrogen atom, a halogen atom, a linear or branched $(C_1-C_{10})$alkyl, an $(C_1-C_{10})$alkoxy, $C_2-C_{10}$ branched or linear alkenyl or $C_2-C_{10}$ branched or linear alkynyl, an $(C_5-C_{14})$aryl, and an $(C_5-C_{14})$ aryloxy group, in which said group is optionally substituted by at least one halogen atom, hydroxyl or $-NH_2$ group;

and wherein R represents

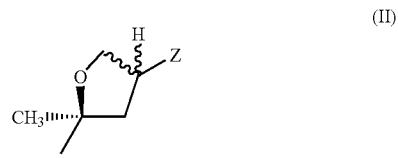

(II)

in which Z represents

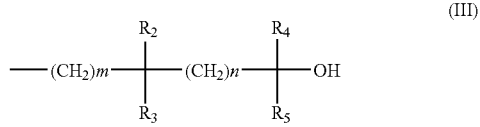

(III)

wherein:
$R_2$ and $R_3$, identical or different, represent a group selected from H, halogen atom, a $C_1-C_{10}$ branched or linear alkyl, $C_2-C_{10}$ branched or linear alkenyl or $C_2-C_{10}$ branched or linear alkynyl group; $R_4$ and $R_5$, identical or different, represent a group selected from H, halogen atom, a $C_1$-$C_6$ linear or branched alkyl, $C_2$-$C_{10}$ branched or linear alkenyl or $C_2$-$C_{10}$ branched or linear alkynyl group;

m represents an integer comprised between 0 and 5 inclusive; and n represents an integer comprised between 0 and 5 inclusive.

The invention also includes the optical and geometrical isomers of said compounds, the racemates, salts, hydrates and the mixtures thereof.

The compounds of the invention possess several chiral centers and may thus exist in optically active forms. The R- and S-isomers and mixtures thereof, including racemic mixtures are contemplated by this invention.

Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

The alkyl groups may be linear or branched. Examples of alkyl groups having from 1 to 10 carbon atoms inclusive are methyl, ethyl, propyl, isopropyl, t-butyl, n-butyl, pentyl, hexyl, heptyl, octyl, nonyl, decyl, 2-ethylhexyl, 2-methylbutyl, 2-methylpentyl, 1-methylhexyl, 3-methylheptyl and the other isomeric forms thereof. Preferably, alkyl groups present from 1 to 6 carbon atoms.

The alkenyl groups are linear or branched hydrocarbon functions containing one or more double bonds, such as for instance the allyl group. They advantageously contain from 2 to 6 carbon atoms and, preferably, 1 or 2 double bonds. Alkenyl groups may be substituted by an aryl group such as defined hereinabove, in which case it is called an arylalkenyl group.

The alkynyl groups are linear or branched hydrocarbon functions containing one or more triple bonds, such as for instance the 3-(benzyloxy)prop-1-ynyl, phenylethynyl, prop-2-ynyl and tert-butyl-prop-2-ynylcarbamate groups. They advantageously contain from 2 to 6 carbon atoms and, preferably, 1 or 2 double bonds. Alkynyl groups may be substituted by an aryl group such as defined hereinabove, in which case it is called an arylalkynyl group.

Within the context of the present application, the term alkoxy denote a linear or branched saturated group containing from 1 to 10, preferably from 1 to 6, carbon atoms. An alkoxy group is specifically an —O-alkyl group, wherein the alkyl group is as defined above.

The term aryl includes any aromatic group comprising from 5 to 14 carbon atoms, preferably from 6 to 14 carbon atoms, optionally interrupted by one or several heteroatoms selected from N, O, S or P (termed, more specifically, heteroaryl). Most preferred aryl groups are mono- or bi-cyclic and comprises from 6 to 14 carbon atoms, such as phenyl, α-naphtyl, β-naphtyl, antracenyl, or fluorenyl group.

The term aryloxy denotes an —O-aryl group, wherein the aryl group is as defined above.

Halogen is understood to refer to fluorine, chlorine, bromine or iodine.

In a particular embodiment, $R_1$ represents a group selected from H, halogen atom, $CH_3$, $(CH_2)_3OH$ or $O(CH_2)_3OH$ and most preferably $R_1$ is H or $CH_3$.

As represented by formula (I), R can represent either

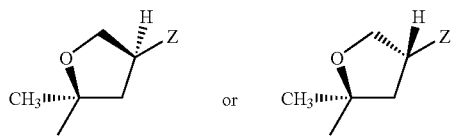

More preferably, R represents:

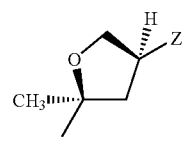

In a particular embodiment, m represents an integer 0, 1, 2, 3, 4 or 5. More preferably, m is 0 or 1.

In a particular embodiment, n represents an integer 0, 1, 2, 3, 4 or 5. More preferably, n is 0.

In a particular embodiment, $R_2$ and $R_3$, identical or different, represent a group selected from H, halogen atom and a $C_1$-$C_4$ branched or linear alkyl. More preferably, both represent H or halogen atom.

In a particular embodiment, $R_4$ and $R_5$, identical or different, represent a group selected from H, halogen atom and a $C_1$-$C_4$ linear or branched alkyl. More preferably, at least one of $R_4$ and $R_5$ is different from H, in particular at least one is $CH_3$ (for instance one is H and the other one is $CH_3$). More specifically, both represent $CH_3$.

As represented by formula (I) above, compounds of the invention may present the following formulas:

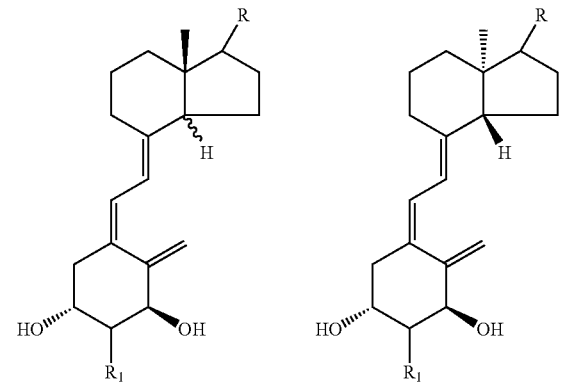

A preferred embodiment of the present invention relates to compounds having the formula (IV):

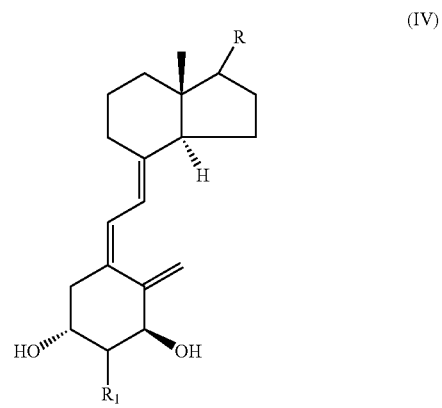

(IV)

In a most preferred embodiment, the invention relates to two particular analogs of 1α,25(OH)2D₃, named compounds A and B, which present a formula (IV) as described above and wherein R, in the general formula (IV), corresponds to:

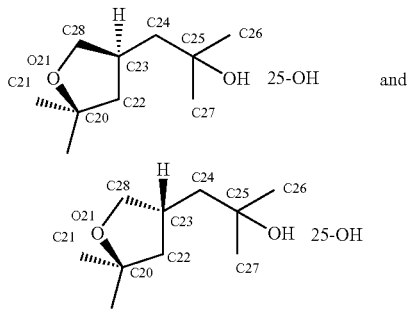

respectively.

Compounds A and B are two diastereoisomers. Compound A exhibits a VDR superagonist activity while compound B behaves like 1α,25(OH)₂D₃.

When the compounds of formula (I) according to the invention are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, perchloric, and the like. Representative examples of suitable organic acids include formic, acetic, trichloroacetic, trifluoroacetic, propionic, benzoic, cinnamic, citric, fumaric, and the like. Further examples of pharmaceutically acceptable inorganic or organic acid addition salts include the pharmaceutically acceptable salts listed in J. Pharm. Sci. 1977, 66, 2, and in Handbook of Pharmaceutical Salts: Properties, Selection, and Use edited by P. Heinrich Stahl and Camille G. Wermuth 2002. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamineoline and the like.

Another aspect of the present invention relates to a method for preparing the compounds as defined above. The compounds of the invention may be prepared from commercially available products, employing a combination of chemical reactions known to those skilled in the art.

In a particular embodiment, compounds A and B of the present invention may be prepared by implementing the following synthesis route:

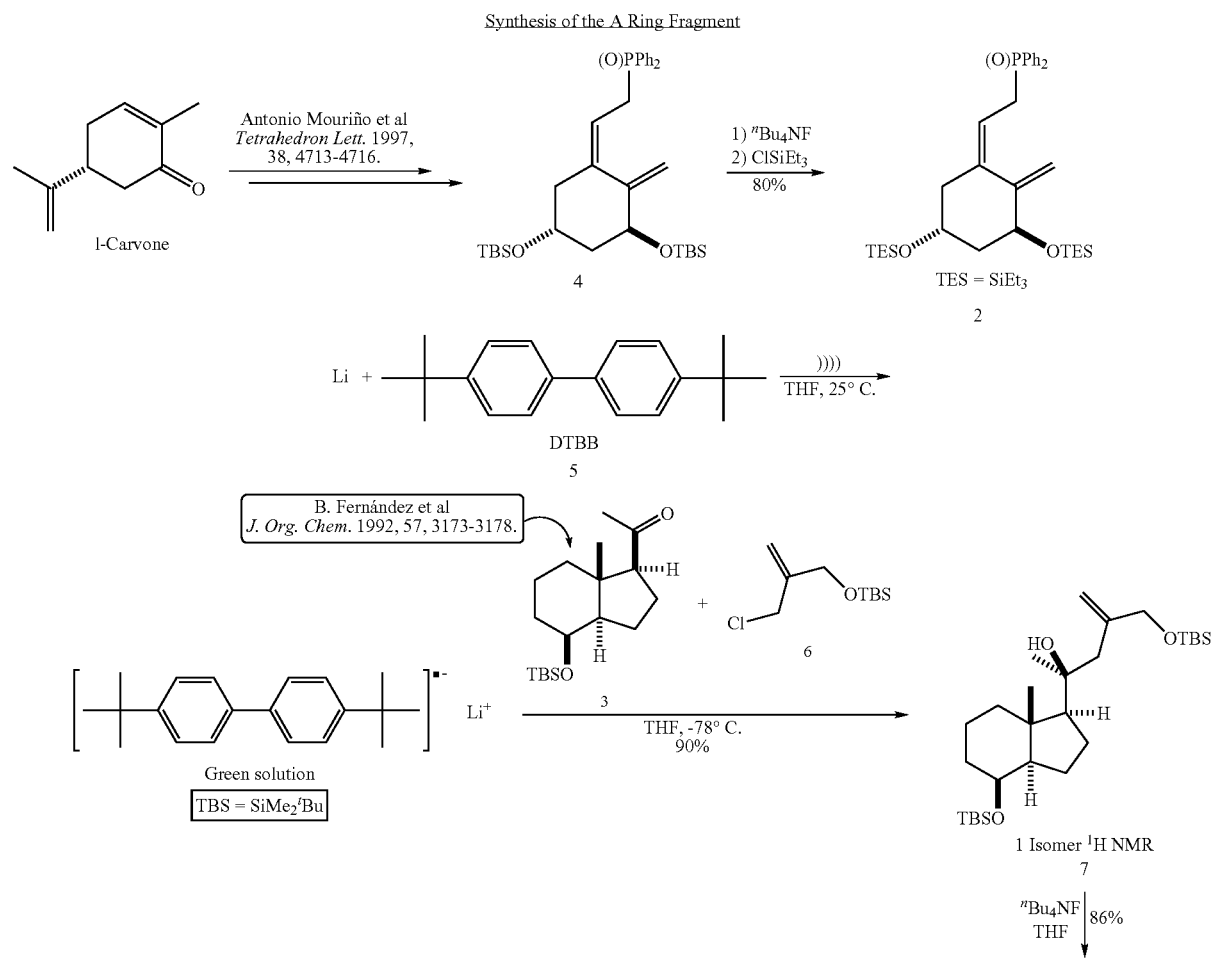

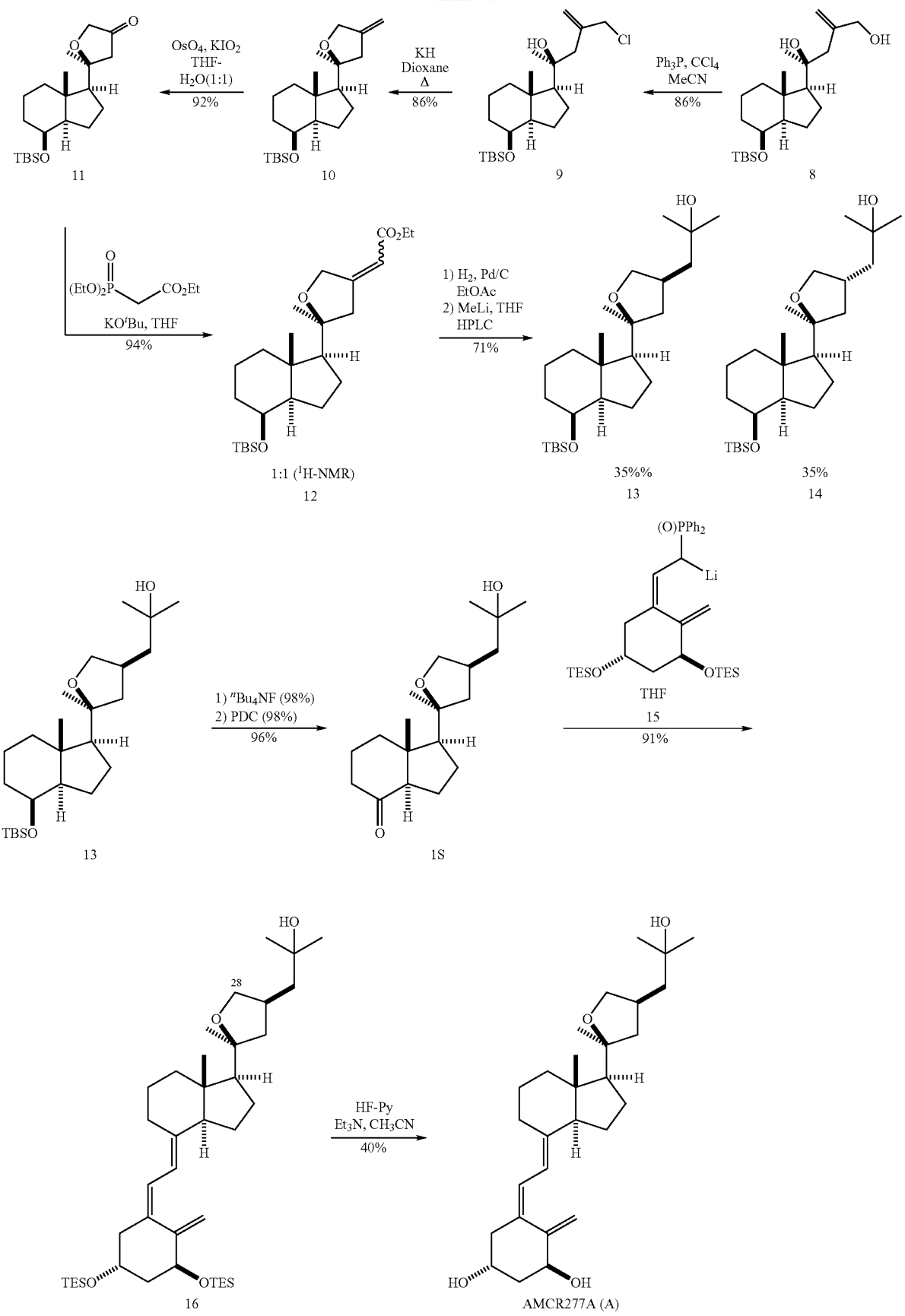

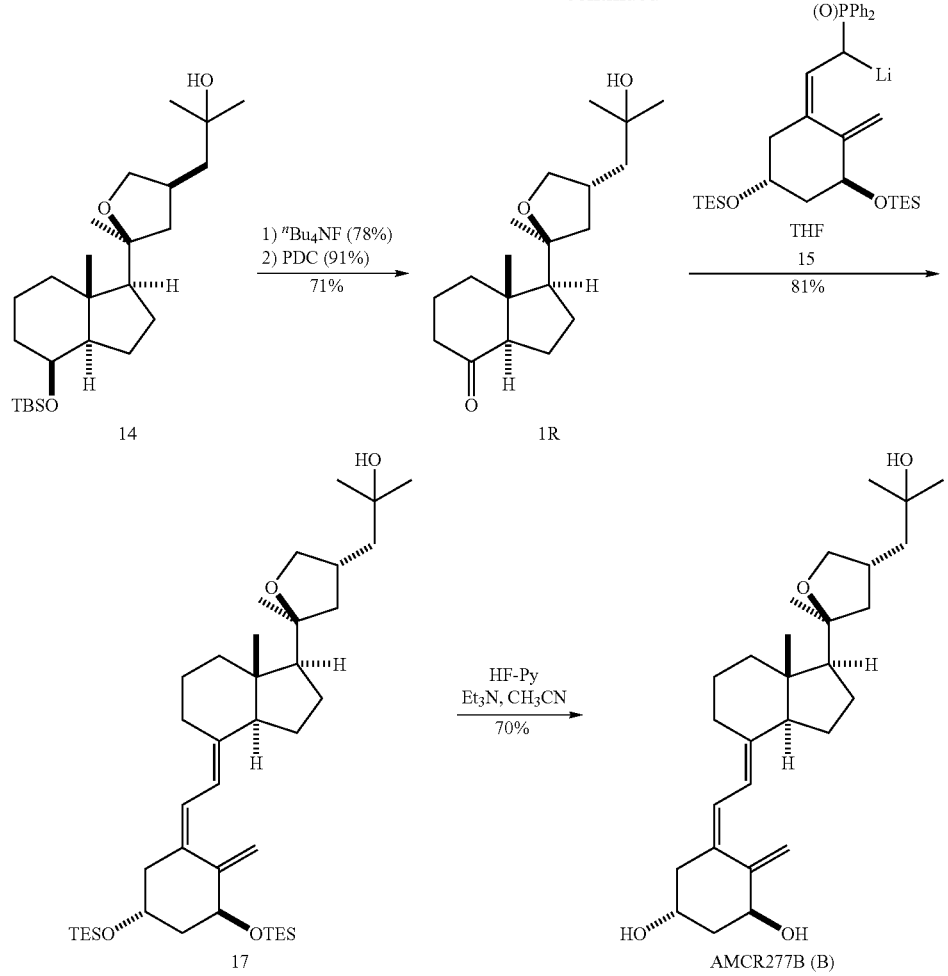

Following guidance contained in this application, one skilled in the art knows how to adapt this process to prepare other compounds according to formula (I).

The present invention also relates to pharmaceutical compositions comprising at least one compound as defined above in a pharmaceutically acceptable support, optionally in association with another active agent.

Another aspect of the invention is to use the compounds of the invention to treat disease states responsive to Vitamin D receptor ligands.

A further aspect of the invention relates to the use of a compound as defined above for the manufacture of a medicament for use in the treatment of disease states responsive to Vitamin D receptor ligands, in particular cancer, dermatological disorders, inflammation related disorders, autoimmune diseases, osteodistrophy or osteoporosis.

The invention relates more particularly to pharmaceutical compositions for the treatment of cancer (including breast, prostate, colon cancer, or leukemia), inflammation related disorders (including rheumatoid arthritis, or psoriatic arthritis), dermatological disorders (including psoriasis or photoaging), autoimmune diseases (including multiple sclerosis or type I diabetes), osteodistrophy or osteoporosis, especially low bone turnover osteoporosis, steroid induced osteoporosis, senile osteoporosis or postmenopausal osteoporosis, osteomalacia or renal osteodystrophy.

The invention further concerns a method for the treatment of disease states responsive to Vitamin D receptor ligands, including in particular cancer (including breast, prostate, colon cancer, or leukemia), inflammation (including rheumatoid arthritis, or psoriatic arthritis), dermatological disorders (including psoriasis or photoaging), autoimmune diseases (including multiple sclerosis or type I diabetes), osteodistrophy or osteoporosis (including low bone turnover osteoporosis, steroid induced osteoporosis, senile osteoporosis or postmenopausal osteoporosis, osteomalacia or renal osteodystrophy), comprising administering to a subject, in particular human, in need of such treatment, an effective dose of a compound represented by formula (I) or of a pharmaceutical composition according to the invention.

The treatment may be topical, transdermal, oral, rectal, sublingual, intranasal or parenteral. The compounds can be administered by injection or by intravenous infusion or suitable sterile solutions, or in the form of liquid or solid doses via the alimentary canal, or in the form of creams, ointments, patches, or similar vehicles suitable for transdermal applications. The compounds may be present in a composition in an amount from about 0.01 µg/g to about 500 µg/g of the composition, and may be administered in dosages of from about 0.1 µg/day to about 50 µg/day and more specifically from about 0.5 µg/day to about 2 µg/day.

The compounds may be formulated as solutions in pharmaceutically compatible solvents or as emulsions, suspensions or dispersions in suitable pharmaceutical solvents or vehicle, or as pills, tablets or capsules that contain solid vehicles in a way known in the art. For topical use, the compounds are preferably formulated as creams or ointments or in a similar pharmaceutical form suitable for topical use. Topical administration includes liquid or semi-liquid preparations such as liniments, lotions, applicants, oil-in-water or water-in-oil emulsions such as creams, ointments or pastes; or solutions or suspensions such as drops; or as sprays. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations for rectal administration may be in the form of a suppository incorporating the active ingredient and carrier such as cocoa butter, or in the form of an enema. Formulations suitable for parenteral administration conveniently comprise a sterile oily or aqueous preparation of the active ingredient which is preferably isotonic with the blood of the recipient.

Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

The compounds are advantageously applied by injection or intravenous infusion of suitable sterile solutions or as oral dosage by the digestive tract or topically in the form of creams, ointments, lotions or suitable transdermal plasters.

By "effective amount" it is meant that quantity of pharmaceutical agent corresponding to formula (I) which prevents, removes or reduces the deleterious effects of a disease state in mammals, including humans. It is understood that the administered dose may be adapted by those skilled in the art according to the patient, the pathology, the mode of administration, etc.

Whenever within this whole specification "treatment of a condition or disorder" or the like is mentioned with reference to a compound of formula (I), there is meant:
a) a method for treating a condition or disorder, said method comprising administering a compound of the invention to a subject in need of such treatment;
b) the use of a compound of the invention for the treatment of a condition or a disorder;
c) the use of a compound of the invention for the manufacture of a pharmaceutical preparation for the treatment of a condition or a disorder; and/or
d) a pharmaceutical preparation comprising a dose of a compound of the invention that is appropriate for the treatment of a condition or a disorder.

Within the context of the invention, the term treatment denotes curative, symptomatic, and preventive treatment. Compounds of the invention can be used in humans with existing disease, including at early or late stages of progression of the disease. The compounds of the invention will not necessarily cure the patient who has the disease but will delay or slow the progression or prevent further progression of the disease, ameliorating thereby the patients' condition. The compounds of the invention can also be administered to those who do not have the diseases but who would normally develop the disease or be at increased risk for the disease, they will not develop the disease. Treatment also includes delaying the development of the disease in an individual who will ultimately develop the disease or would be at risk for the disease due to age, familial history, genetic or chromosomal abnormalities, and/or due to the presence of one or more biological markers for the disease, such as a known genetic mutation in tissues or fluids. By delaying the onset of the disease, compounds of the invention have prevented the individual from getting the disease during the period in which the individual would normally have gotten the disease or reduce the rate of development of the disease or some of its effects but for the administration of compounds of the invention up to the time the individual ultimately gets the disease. Treatment also includes administration of the compounds of the invention to those individuals thought to be predisposed to the disease. In treating the above diseases, the compounds of the invention are administered in a therapeutically effective amount.

Such compounds, compositions comprising the same, or treatment can be implemented alone or in combination with other active ingredients, compositions or treatments. The compounds may be suitably administered alone, or together with graded doses of another active ingredient, such as vitamin D compound, e.g. 1α-hydroxyvitamin D2 or D3, or 1α,25-dihydroxyvitamin D3, in situations where different degrees of bone mineral mobilization and calcium transport stimulation is found to be advantageous. Moreover, it can correspond to treatment of chronic or acute disorders.

Further aspects and advantages of this invention will be disclosed in the following examples, which should be regarded as illustrative and not limiting the scope of this application.

LEGENDS TO THE FIGURES

FIG. 1: Chemical structures of known ligand 1α,25(OH)$_2$D$_3$ and new ligands (compounds A and B)

Figure 2:
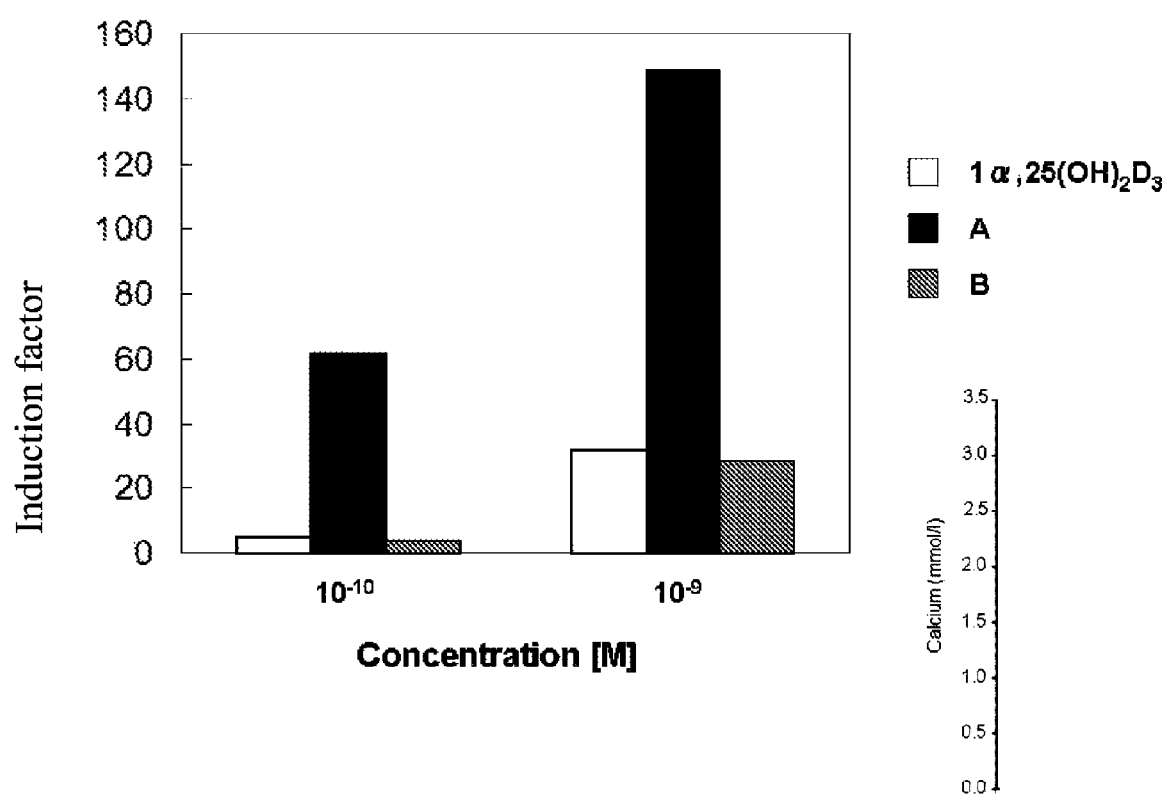

FIG. 2: Transcriptional activation of VDR by 1α,25(OH)$_2$D$_3$, compound A and compound B. 293 EBNA cells were transiently transfected with a UAS-TATA-luciferase reporter plasmid and an expression plasmid of GAL4 DBD-VDR LBD and subsequently treated with 1α,25(OH)$_2$D$_3$, compound A (A), and compound B (B) at $10^{-10}$ and $10^{-9}$M. Luciferase activity for each sample was normalized to the β-galactosidase activity. Data is shown as fold induction of agonist induced luciferase activity divided by luciferase activity of vehicle.

Figure 3:
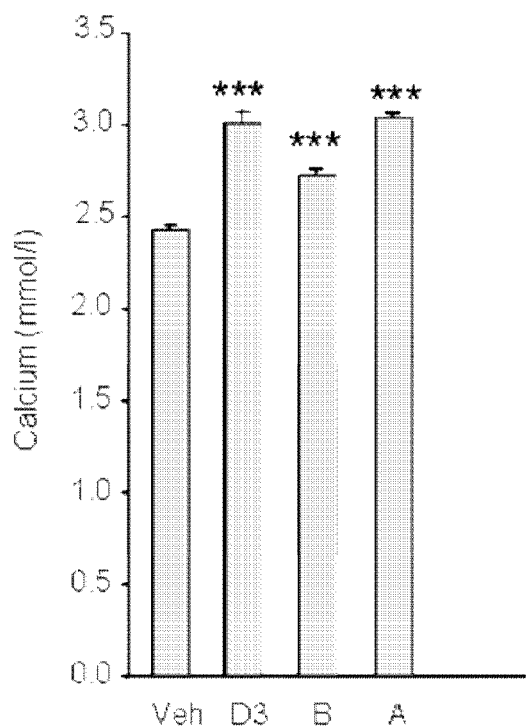
Figure 3:
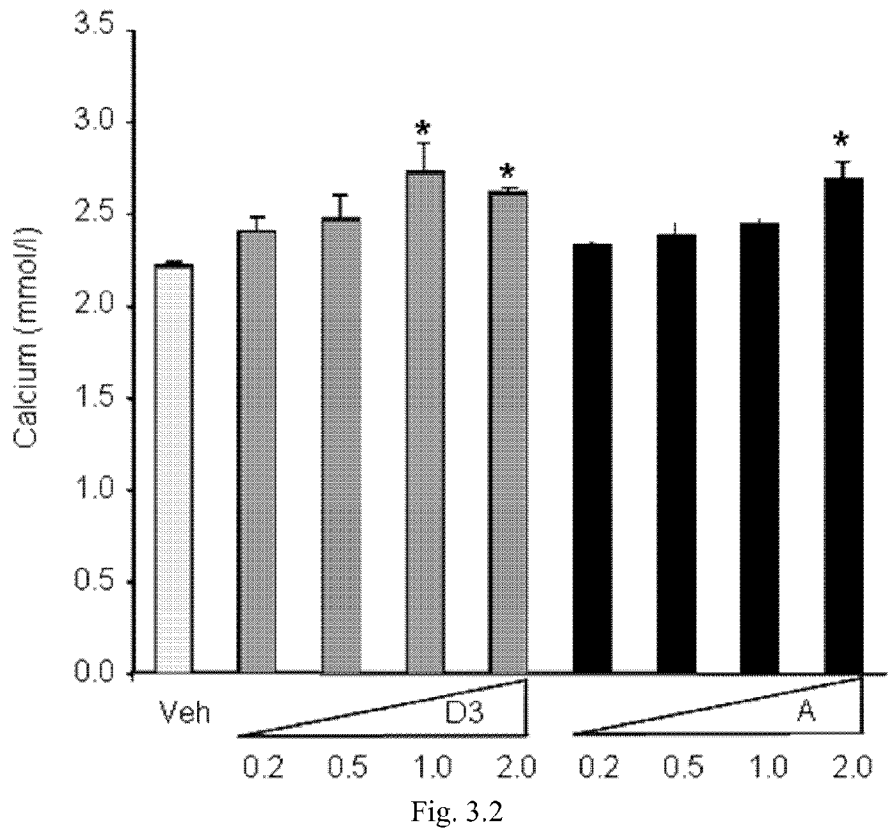

FIG. 3: Effects of 1α,25(OH)$_2$D$_3$ and new ligands (compounds A and B) on calcium levels in serum. (FIG. 3.1) Mice were fed either with vehicle (sesame oil), 1α,25(OH)$_2$D$_3$ 2 µg/kg, 2 µg/kg compound A or 2 µg/kg compound B during 7 days. (FIG. 3.2) Mice were fed either with vehicle (Veh), 1α,25(OH)$_2$D$_3$ (D3), or compound A during 4 days. Data are presented as mean±SEM. Significant differences are marked as *p<0.05, ***p<0.01.

EXAMPLES

I. Compounds A and B Synthesis

All reactions involving oxygen- or moisture-sensitive compounds were carried out under a dry Ar atmosphere. Reaction temperatures refer to external bath temperatures. All dry solvents were distilled under Ar immediately prior to use. Tetrahydrofurane (THF) was distilled from Na/benzophenone; dichloromethane (CH$_2$Cl$_2$) was distilled from P$_2$O$_5$; acetonitrile (CH$_3$CN), i-Pr$_2$NH, Et$_3$N and i-Pr$_2$NEt were distilled from CaH$_2$. Liquid reagents or solutions of reagents were added by syringe or cannula. Organic extracts were dried over anhydrous Na$_2$SO$_4$, filtered and concentrated using a rotary evaporator at aspirator pressure (20-30 mm Hg). Reactions were monitored by thin-layer chromatography (TLC) using aluminium-backed Merck 60 silica gel plates (0.2 mm thickness); the chromatograms were visualized first with ultraviolet light (254 nm) and then by immersion in a solution of phosphomolybdic acid in EtOH (5%), followed by heating. Flash column chromatography was performed with Merck 60 (230-400 mesh) silica gel. All NMR spectra were measured with solutions in CDCl$_3$ unless otherwise stated. Chemical shifts are reported on the δ scale (ppm) downfield from tetramethylsilane (δ=0.0 ppm) using the residual solvent signal at δ=7.26 ppm ($^1$H) or δ=77 ppm ($^{13}$C) as internal standard; coupling constants are reported in Hz. Distortionless Enhancement by Polarization Transfer (DEPT) was used to assign carbon types.

[(2Z)-2-[(3S,5R)-5-Bis [triethylsilyl]-2-methyl-enecyclohexylidene]-ethyl]diphenylphosphine Oxide)(2)

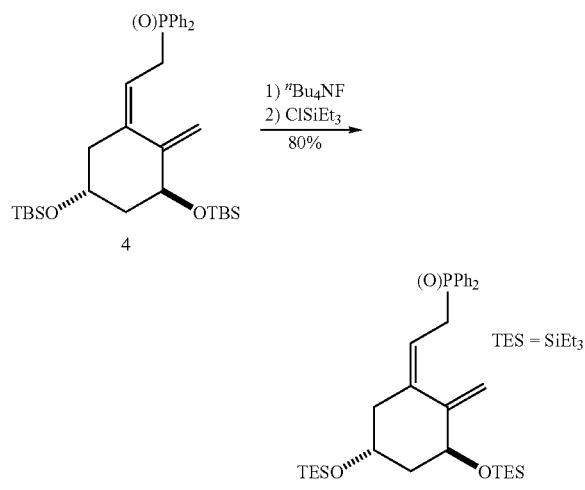

The residue was purified by flash chromatography (SiO$_2$, 3×10 cm, 15% EtOAc-hexanes) to give 2 (1.78 g, 80%, colorless oil).

$^1$H-NMR (250 MHz, CDCl$_3$, δ, ppm): 7.59~7.68 [m, 4H, (O)PPh$_2$], 7.26~7.43 [m, 6H, (O) PPh$_2$], 5.10~5.25 (m, 2H), 4.81 (s, 1H), 4.30 (m, 0.73H), 4.03~4.08 (m, 0.83H), 3.35~3.48 (m, 1H), 3.02~3.15 (m, 1H), 2.36 (d, J=11.8 Hz, 1H), 1.97~2.10 (m, 2.42H), 1.67~1.75 (m, 1.2H), 1.19~1.21 (m, 1.86H).

$^{13}$C-NMR (62.89 MHz, CDCl$_3$, δ, ppm): 4.60 (CH$_2$), 4.64 (CH$_2$), 6.72 (CH$_3$), 6.75 (CH$_3$), 30.88 (CH$_2$), 32.00 (CH$_2$), 44.89 (CH$_2$), 45.46 (CH$_2$), 67.06 (CH), 70.38 (CH), 110.35 (CH$_2$), 115.12 (CH), 115.24 (CH), 128.28 (CH), 128.46 (CH), 130.85 (CH), 130.95 (CH), 130.99 (CH), 131.09 (CH), 131.57 (CH), 131.92 (C), 133.48 (C), 140.75 (C), 140.95 (C), 147.61 (C).

MS [m/z, (%)]: 582.31 (100), 583.31 (45.8), 584.31 (10.6), 584.32 (7.1), 585.31 (2.9), 585.32 (1.7)

(S)-4-(tert-butyldimethylsilyloxy)-2-((3S,3aS,7S,7aR)-octahydro-7-(tert-butyldimethylsilyloxy)-3a-methyl-1H-inden-3-yl)pent-4-en-2-ol (7)

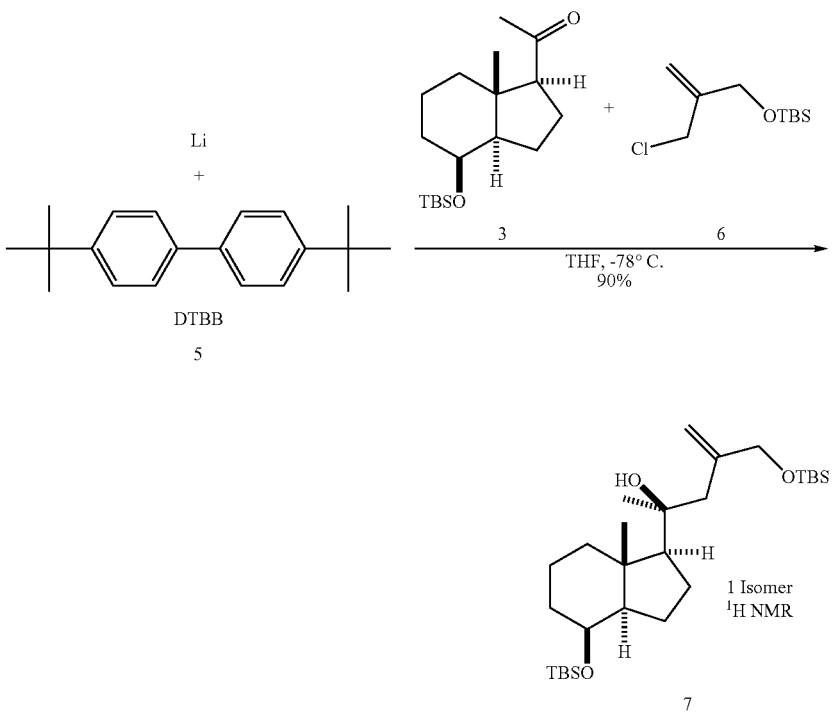

A solution of 4 (2.23 g, 3.82 mmol) in dry THF (20 mL) was treated with $^n$Bu$_4$NF (3.2 g, 10 mmol). After concentration the residue was extracted with CH$_2$Cl$_2$ (3×20 mL). The organic phase was dried, filtered and concentrated in vacuum. The residue was dissolved in dry pyridine (10 mL) and treated with ClSiEt$_3$ (1.5 g, 9.9 mmol) and DMAP (4-dimethylaminopyridine, 20 mg). After 15 min, the reaction was quenched by the addition of a saturated solution of NaHCO$_3$ (20 mL). The mixture was extracted with CH$_2$Cl$_2$ (2×30 ml). The organic phase was dried, filtered and concentrated in vacuum.

TBS Stands for "tert-butyldimethylsilyl".

Lithium (330 mg, 47.55 mmol) was cut into small portions and added to a solution. 4,4'-di-tert-butyl-biphenyl (DTBB, 1.3 g, 4.88 mmol) in dry tetrahydrofuran (THF, 40 mL) under argon. After sonication for 40 min green color was observed. The mixture was cooled to −78° C. A solution of 3 (B. Fernández, J. A. Martinez-Pérez, J. R. Granja, L. Castedo, and A. Mouriño *J. Org. Chem.* 1992, 57, 3173-3178) (0.7 mg, 2.25 mmol) and 6 (M. Sworin and K.-C. Lin, *J. Am. Chem. Soc.* 1989, 111, 1815) (2.9 g, 11.36 mmol) in dry THF (15 mL) was slowly added. The green color change to red color. The reaction was quenched by the addition of methanol (1 mL). Et₂O (30 mL) and H₂O (30 mL) were successively added. The organic phase was extracted with Et₂O (2×30 mL). The combine organic phase was dried (Na₂SO₄), filtered and concentrated in vacuum. The residue was purified by flash chromatography (SiO₂, 2.5×11 cm, Hexanes) to give 7 (1.3 g, 95%, colorless oil).

¹H-NMR (250 MHz, CDCl₃, δ, ppm): 0.00 (s, 6H, TBS), 0.08 (s, 6H, TBS), 0.88 (s, 9H, TBS), 0.92 (s, 9H, TBS), 1.11 (s, 3H), 1.23 (s, 3H), 4.04 (m, 1H, HC—OTBS), 4.14 (s, 2H, H₂C—OTBS), 4.86 (s, 1H, CH₂=), 5.16 (s, 1H, CH₂=).

¹³C-NMR (62.89 MHz, CDCl₃, δ, ppm): −5.35 (CH₃), −4.83 (CH₃), 15.42 (CH₃), 17.62 (CH₂), 17.99 (C), 18.34 (C), 21.84 (CH₂), 22.82 (CH₂), 25.78 (CH₃), 25.91 (CH₃), 26.06 (CH₃), 34.34 (CH₂), 41.21 (CH₂), 43.02 (C), 47.04 (CH₂), 53.08 (CH), 60.55 (CH), 67.37 (CH₂), 69.49 (CH), 74.26 (C), 114.33 (CH₂), 145.32 (C)

MS [m/z, (%)]: 496.38 (100.0), 497.38 (41.2), 498.38 (8.5), 498.37 (6.7), 499.38 (2.9)

(S)-4-((3S,3aS,7S,7aR)-octahydro-7-(tert-butyldimethylsilyloxy)-3a-methyl-1H-inden-3-yl)-2-methyl-enepentane-1,4-diol (8)

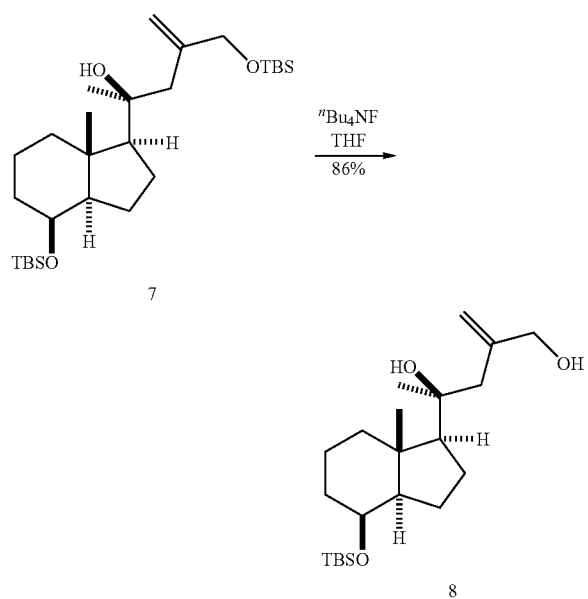

A solution of 7 (1.3 g, 2.6 mmol) in dry THF (6 mL) was treated with a ⁿBu₄NF (1.6 g, 5 mmol). After 1 h, a saturated solution of NaHCO₃ (30 mL) was added. The mixture was extracted with EtOAc (3×30 mL). The organic phase was dried, filtered and concentrated in vacuum. The residue was purified by flash chromatography (SiO₂, 3×10 cm, 25% Et₂O-hexanes) to give 8 (0.86 g, 86%, white solid, mp: 95° C.), Elementary analysis: C=68.12%, H=11.18%

¹H-NMR (250 MHz, CDCl₃, δ, ppm): 0.00 (ds, 6H, CH₃Si×2), 0.88 (s, 9H, ᵗBuSi), 1.13 (s, 3H, CH₃-Cy), 1.27 (s, 3H, CH₃C—OH), 4.00-4.08 (m, 3H, CH₂OH, CH—OTBS), 4.83 (s, 1H, C=H₂), 4.10 (s, 1H, C=H₂).

¹³C-NMR (62.89 MHz, CDCl₃, δ, ppm): −5.22 (CH₃), −4.86 (CH₃), 15.50 (CH₃), 17.51 (CH₂), 17.94 (C), 21.68 (CH₂), 22.71 (CH₂), 25.74 (CH₃), 25.74 (CH₃), 34.18 (CH₂), 41.08 (CH₂), 43.04 (C), 47.04 (CH₂), 52.91 (CH), 60.58 (CH), 67.12 (CH₂), 69.35 (CH), 75.26 (C), 116.18 (CH₂), 145.43 (C)

MS [m/z, (%)]: 496.38 (100.0), 497.38 (41.2), 498.38 (8.5), 498.37 (6.7), 499.38 (2.9)

Elementary Analysis Calculated for C₂₂H₄₂O₃Si: C, 69.05; H, 11.06; O, 12.54; Si, 7.34. Found: C, 68.13; H, 11.18

(S)-4-(chloromethyl)-2-((3S,3aS,7S,7aR)-octahydro-7-(tert-butyldimethylsilyloxy)-3a-methyl-1H-inden-3-yl)pent-4-en-2-ol (9)

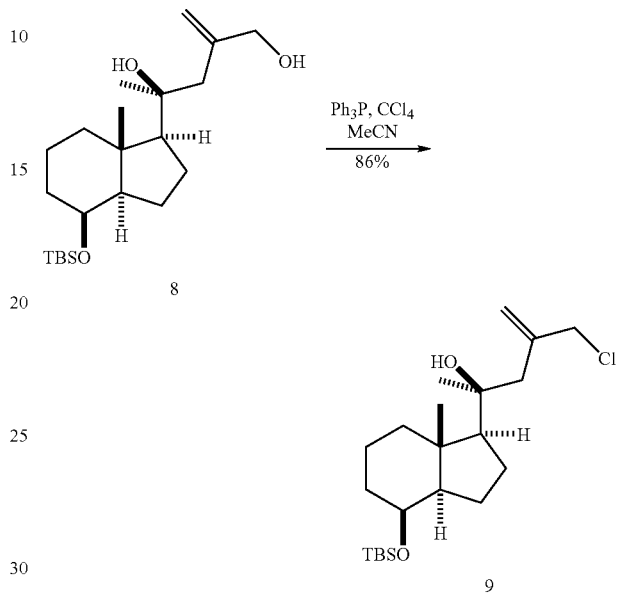

A mixture of 8 (82 mg, 0.2 mmol), Ph₃P (85 mg, 3.32 mmol), CCl₄ (54 mg, 0.35 mmol, dried with CaCl₂), and CH₃CN (2 mL, dried with CaH₂) was stirred for 30 min under argon. The mixture was flash chromatographed (SiO₂, 2.5×5 cm. 5% EtOAc-hexanes) to give 9 (70 mg, 77%). This unstable compound was immediately used in the next step.

¹H-NMR (250 MHz, CDCl₃, δ, ppm): 0.00 (ds, 6H, CH₃Si×2), 0.88 (s, 9H, ᵗBuSi), 1.12 (s, 3H, CH₃-Cy), 1.25 (s, 3H, CH₃C—OH), 4.00-4.02 (m, 1H, CH—OTBS), 4.10 (d, J=11.6 Hz, 1H CH₂—Cl), 4.29 (d, J=11.6 Hz, 1H CH₂—Cl), 5.0 (s, 1H, C=H₂), 5.3 (s, 1H, C=H₂).

¹³C-NMR (62.89 MHz, CDCl₃, δ, ppm): −5.18 (CH₃), −4.80 (CH₃), 15.56 (CH₃), 17.56 (CH₂), 17.99 (C), 21.78 (CH₂), 22.76 (CH₂), 25.78 (CH₃), 25.78 (CH₃), 34.22 (CH₂), 41.10 (CH₂), 43.05 (C), 45.61 (CH₂), 49.67 (CH₂), 52.97 (CH), 60.28 (CH), 69.37 (CH), 75.39 (C), 118.57 (CH₂), 142.58 (C)

(S)-tetrahydro-2-((3S,3aS,7S,7aR)-octahydro-7-(tert-butyldimethylsilyloxy)-3a-methyl-11H-inden-3-yl)-2-methyl-4-methylenefuran (10)

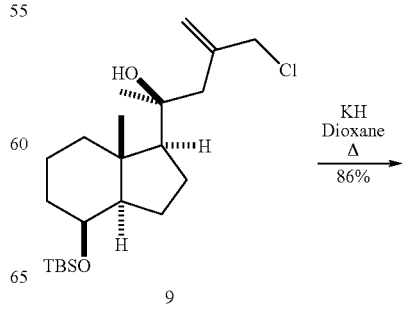

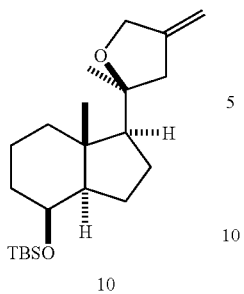

10

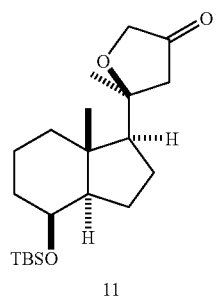

11

A solution of 9 (0.5 g, 1.32 mmol) in dry dioxane (5 mL), was treated with KH (0.3 g, 7.5 mmol). The mixture was heated at reflux. After 30 min, the reaction was quenched by the addition of methanol (1 mL) and H$_2$O (10 mL). The mixture was extracted with Et$_2$O (3×15 mL). The combined organic phase was dried, filtered and concentrated in vacuum. The residue was purified by flash chromatography (SiO$_2$, 2.5×7 cm, hexanes) to give 10 (0.4 g, 86%, colorless oil). 1H-NMR-13C-NMR. HRMS (FAB)

$^1$H-NMR (250 MHz, CDCl$_3$, δ, ppm): 0.00 (ds, 6H, CH$_3$Si×2), 0.87 (s, 9H, $^t$BuSi), 1.10 (s, 3H, CH$_3$-Cy), 1.21 (s, 3H, CH$_3$C—O), 2.38 (d, 1H, J=13.5 Hz, CH$_2$—C=), 2.11 (d, 1H, J=13.5 Hz, CH$_2$—C=), 4.34 (m, 2H=C—CH$_2$—O), 4.01 (m, 1H, CH—OTBS), 4.92 (s, 1H, C=H$_2$), 5.14 (s, 1H, C=H$_2$)

$^{13}$C-NMR (62.89 MHz, CDCl$_3$, δ, ppm): −5.21 (CH$_3$), −4.85 (CH$_3$), 15.63 (CH$_3$), 17.57 (CH$_2$), 17.97 (C), 22.26 (CH$_2$), 22.90 (CH$_2$), 24.70 (CH$_3$), 25.77 (CH$_3$), 34.38 (CH$_2$), 40.89 (CH$_2$), 42.77 (C), 44.42 (CH$_2$), 52.92 (CH), 59.21 (CH), 69.38 (CH), 69.84 (CH$_2$), 85.58 (C), 103.99 (CH$_2$), 148.77 (C)

MS [m/z, (%)]: 105.06 (44.23), 107.07 (50.80), 109.09 (23.70), 115.09 (29.42), 119.08 (36.92), 121.10 (36.07), 131.08 (24.96), 133.10 (55.50), 135.12 (67.29), 159.13 (31.40), 161.14 (67.45), 171.13 (92.61), 201.17 (25.35), 213.17 (58.40), 231.18 (43.82), 363.27 (100.00), 364.28 (31.41), 379.27 (34.03), (S)-dihydro-5-((3S,3aS,7S,7aR)-octahydro-7-(tert-butyldimethylsilyloxy)-3a-methyl-1H-inden-3-yl)-5-methylfuran-3(2H)-one (11)

Alkene 10 (140 mg, 0.38 mmol), in THF/H$_2$O (40 mL, 1:1) was treated with sodium periodate (415 mg, 1.8 mmol) and a solution of osmium tetroxide in H$_2$O (0.2 mL, 4%) and left overnight at room temperature. The reaction mixture was treated with a saturated solution of NaCl (40 mL). The mixture was extracted with Et$_2$O (3×50 mL). The combined organic phase was dried, filtered and concentrated in vacuum. The residue was purified by flash chromatography (SiO$_2$, 2.5×8 cm, 5% EtOAc-hexanes) to give 11 (130 mg, 91%, white solid, mp: 52° C.)).

$^1$H-NMR (250 MHz, CDCl$_3$, δ, ppm): 0.00 (s, 6H, CH$_3$Si×2), 0.87 (s, 9H, $^t$BuSi), 1.07 (s, 3H, CH$_3$—CO), 1.34 (s, 3H, CH$_3$-Cy), 2.15 (d, J=17.9 Hz, 1H, CH$_2$—CO), 2.59 (d, J=17.9 Hz, 1H, CH$_2$—CO), 3.99 (d, J=17.5 Hz, 1H, O—CH$_2$—CO), 4.00 (m, 1H, HC—OTBS), 4.09 (d, J=17.5, 1H, O—CH$_2$—CO).

$^{13}$C-NMR (62.89 MHz, CDCl$_3$, δ, ppm): −5.19 (CH$_3$), −4.83 (CH$_3$), 15.87 (CH$_3$), 17.49 (CH$_2$), 17.98 (C), 22.32 (CH$_2$), 22.77 (CH$_2$), 25.21 (CH$_3$), 25.77 (CH$_3$), 34.25 (CH$_2$), 40.85 (CH$_2$), 42.89 (C), 48.64 (CH$_2$), 52.87 (CH), 59.15 (CH), 69.22 (CH), 69.92 (CH$_2$), 84.80 (C), 216.53 (C).

MS [m/z, (%)]: 133.1 (49.50), 135.1 (63.31), 136.0 (46.33), 137.0 (39.60), 154.1 (20.35), 161.1 (100), 171.1 (73.46), 176.1 (21.68), 199.1 (25.37), 221.1 (22.8), 225.2 (18.55), 233.1 (28.22), 235.2 (16.04), 265.2 (12.96), 291.2 (19.14), 307.1 (6.55), 309.2 (11.30), 363.2 (29.53), 365.2 (67.50), 366.24 (24.74), 367.2 (32.01), 462.2 (28.50).

(Z)-ethyl 2-((S)-dihydro-5-((3S,3aS,7S,7aR)-octahydro-7-(tert-butyldimethylsilyloxy)-3a-methyl-1H-inden-3-yl)-5-methylfuran-3(2H)-ylidene)acetate (12Z) and (E)-ethyl 2-((S)-dihydro-5-((3S,3aS,7S,7aR)-octahydro-7-(tert-butyldimethylsilyloxy)-3a-methyl-1H-inden-3-yl)-5-methylfuran-3(2H)-ylidene)acetate (12E)

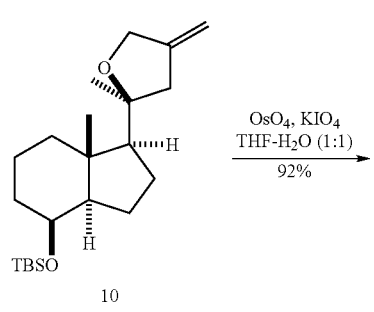

10

OsO$_4$, KIO$_4$
THF-H$_2$O (1:1)
92%
→

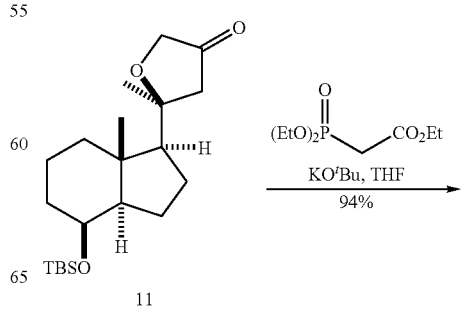

11

(EtO)$_2$P(O)CH$_2$CO$_2$Et
KO$^t$Bu, THF
94%
→

19

-continued

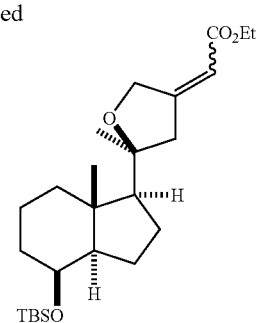

12
1:1 (¹H-NMR)

Dry triethyl phosphonoacetate (2.04 mL, 10.2 mmol) was added dropwise to a stirred solution of potassium tert-butoxide (1.4 g, 10.2 mmol) in dry THF (10 mL). The mixture was stirred at room temperature for 1 h. The mixture was cooled to −8° C. and a solution of 11 (0.6 g, 1.57 mmol) in dry THF (5 mL) was then added. After 1 h at −8° C., a saturated solution of ammonium chloride (10 mL) and H$_2$O (25 mL) were added. The mixture was extracted with Et$_2$O (4×50 mL). The combined organic phase was dried, filtered and concentrated in vacuum. The residue was purified by flash chromatography (SiO$_2$, 2.5×9 cm, 5% Et$_2$O-hexanes) to give 12 (680 mg, 94%, white solid, mp: 101° C.).

Compounds with Minor Polarity:

¹H-NMR (250 MHz, CDCl$_3$, δ, ppm): −0.03 (s, 3H, CH$_3$Si), −0.02 (s, 3H, CH$_3$Si), 0.86 (s, 9H, $^t$BuSi), 1.03 (s, 3H, CH$_3$-Cy), 1.19 (s, 3H, CH$_2$—CO), 1.26 (t, J=7.1 Hz, 3H, CH$_3$—CH$_2$—OCO), 3.99 (m, 1H, HC—OTBS), 4.14 (q, J=7.1 Hz, 2H, CH$_3$—CH$_2$—OCO), 5.73 (m, 1H, H—C=CO$_2$Et).

¹³C-NMR (62.89 MHz, CDCl$_3$, δ, ppm): −5.22 (CH$_3$), −4.86 (CH$_3$), 14.27 (CH$_3$), 15.59 (CH$_3$), 17.52 (CH$_2$), 17.95 (C), 22.19 (CH$_2$), 22.86 (CH$_2$), 24.84 (CH$_3$), 25.75 (CH$_3$), 34.31 (CH$_2$), 40.83 (CH$_2$), 42.79 (C), 43.84 (CH$_2$), 52.86 (CH), 58.95 (CH$_2$), 59.79 (CH), 69.31 (CH), 70.68 (CH$_2$), 86.69 (C), 110.21 (CH), 163.23 (C), 166.42 (C).

Compounds with Major Polarity:

¹H-NMR (250 MHz, CDCl$_3$, δ, ppm): −0.02 (s, 3H, CH$_3$Si), −0.01 (s, 3H, CH$_3$Si), 0.86 (s, 9H, $^t$BuSi), 1.04 (s, 3H, CH$_3$-Cy), 1.18 (s, 3H, CH$_3$—CO), 1.26 (t, J=7.1 Hz, 3H, CH$_3$—CH$_2$—OCO), 2.35 (d, J=16.8 Hz, 1H, CH$_2$C=), 2.77 (d, J=16.8 Hz, 1H, CH$_2$C=), 3.99 (m, 1H, HC—OTBS), 4.13 (q, J=7.1 Hz, 2H, CH$_3$—CH—OCO), 5.77 (s, 1H, H—C=CO$_2$Et).

¹³C-NMR (62.89 MHz, CDCl$_3$, δ, ppm): −5.21 (CH$_3$), −4.85 (CH$_3$), 14.28 (CH$_3$), 15.69 (CH$_3$), 17.52 (CH$_2$), 17.96 (C), 22.24 (CH$_2$), 22.83 (CH$_2$), 24.02 (CH$_3$), 25.76 (CH$_3$), 34.30 (CH$_2$), 40.82 (CH$_2$), 42.76 (C), 45.72 (CH$_2$), 52.88 (CH), 58.63 (CH), 59.92 (CH$_2$), 69.28 (CH), 69.95 (CH$_2$), 84.25 (C), 111.26 (CH), 164.08 (C), 166.08 (C).

Elementary Analysis Calculated for C$_{25}$H$_{44}$O$_4$Si: C, 68.76; H, 10.16; O, 14.65; Si, 6.43. Found: C, 68.71; H, 10.43

MS [m/z, (%)]: 136.04 (28.37) 137.05 (25.77), 141.06 (21.07), 154.06 (26.06), 169.09 (100.00), 305.20 (23.33), 435.28 (29.90), 436.29 (19.78), 437.30 (33.42), 532.27 (16.89).

20

1-((3S,5S)-tetrahydro-5-((3S,3aS,7S,7aR)-octahydro-7-(tert-butyldimethylsilyloxy)-3a-methyl-1H-inden-3-yl)-5-methylfuran-3-yl)-2-methylpropan-2-ol (13)

1-((3R,5S)-tetrahydro-5-((3S,3aS,7S,7aR)-octahydro-7-(tert-butyldimethylsilyloxy)-3a-methyl-1H-inden-3-yl)-5-methylfuran-3-yl)-2-methylpropan-2-ol (14)

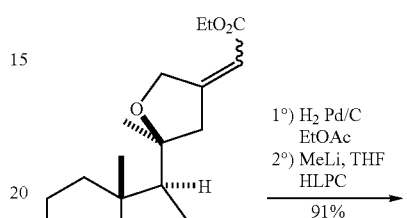

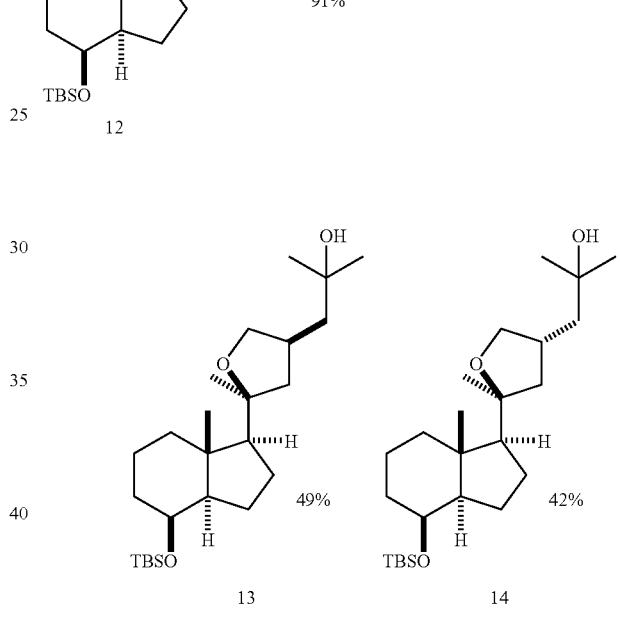

A suspension of 12 (680 mg, 1.56 mmol) and Pd/C$_5$% (15 mg, 0.15 mmol) in EtOAc (20 mL), was stirred in H$_2$ atmosphere (1 atm) for 12 h. The mixture was filtered and concentrated in vacuum. The residue was purified by flash chromatography (SiO$_2$, 2.5×6.5 cm, hexanes) to give 12a (660 mg, 96%, colorless oil).

A solution of MeLi in THF (10 mL, 10 mmol, 1M) was added to a solution of 12a (660 mg, 1.5 mmol) in dry THF (5 mL). The mixture was stirred for 30 min and then warmed to 0° C. over 1 h. MeOH (0.5 mL) and saturated NH$_4$Cl (4 mL) was slowly added. The aqueous layer was extracted with ether (4×30 mL), and the combined organic layer was dried (Na$_2$SO$_4$) and concentrated in vacuum. The residue was purified by HPLC (columna Phenomenex 250×10 mm, 5 Φ-hexane-Et$_2$O) to give 13 (330 mg, 49% in 2 steps) and 14 (280 mg, 42% in 2 steps)

MS [m/z, (%)]: 424.34 (100.0), 425.34 (32.8), 426.34 (5.6), 426.33 (3.3), 427.34 (1.3)

Compounds with Minor Polarity:

¹H-NMR (250 MHz, CDCl$_3$, δ, ppm): −0.04 (s, 3H, CH$_3$Si), −0.03 (s, 3H, CH$_3$Si), 0.85 (s, 9H, $^t$BuSi), 1.00 (s, 3H, CH$_3$-Cy), 1.18 (s, 6H, 2×CH$_3$—C—OH), 1.23 (s, 3H, C H₃—CO), 3.34 (t, J=9 Hz, 1H, OCH₂Cy), 3.97 (m, 1H, HCOTBS), 4.04 (t, 1H, J=7 Hz, OCH₂Cy)

¹³C-NMR (62.89 MHz, CDCl₃, δ, ppm): −5.19 (CH₃), −4.83 (CH₃), 15.04 (CH₃), 17.57 (CH₂), 17.98 (C), 22.25 (CH₂), 22.77 (CH₂), 25.78 (CH₃), 27.53 (CH₃), 29.68 (CH₃), 30.10 (CH₃), 34.40 (CH₂), 35.77 (CH), 40.96 (CH₂), 42.81 (C), 47.14 [2×(CH₂)], 52.96 (CH), 60.12 (CH), 69.40 (CH), 70.93 (C), 73.17 (CH₂), 84.99 (C).

Compounds with Major Polarity:

¹H-NMR (250 MHz, CDCl₃, δ, ppm): −0.02 (s, 3H, CH₃Si), −0.01 (s, 3H, CH₃Si), 0.87 (s, 9H, ᵗBuSi), 1.03 (s, 3H, CH₃-Cy), 1.21 (s, 9H, 2×CH₃—C—OH, CH₃—C—O—CH₂), 3.33 (dd, J=8.5, 9.7, OCH₂Cy), 3.98 (m, 1H, HCOTBS), 4.09 (t, 1H, J=7.8 Hz, OCH₂Cy)

¹³C-NMR (62.89 MHz, CDCl₃, δ, ppm): −5.19 (CH₃), −4.83 (CH₃), 15.53 (CH₃), 17.57 (CH₂), 17.98 (C), 22.21 (CH₂), 22.73 (CH₂), 25.78 (CH₃), 27.14 (CH₃), 29.81 (CH₃), 30.01 (CH₃), 34.13 (CH), 34.38 (CH₂), 40.93 (CH₂), 42.69 (C), 46.08 (CH₂), 46.40 (CH₂), 52.96 (CH), 60.08 (CH), 69.38 (CH), 70.94 (C), 74.88 (CH₂), 85.19 (C).

(1S,3aR,7aR)-octahydro-1-((2S,4S)-tetrahydro-4-(2-hydroxy-2-methylpropyl)-2-methylfuran-2-yl)-7a-methylinden-4-one (1S)

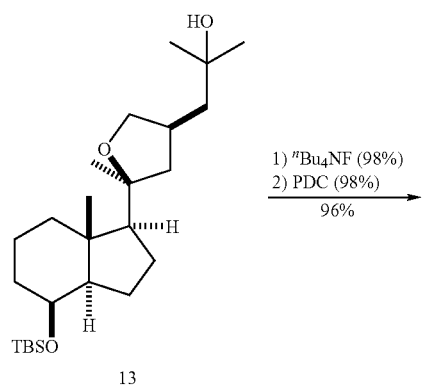

(1S,3aR,4S,7aS)-octahydro-1-((2S,4S)-tetrahydro-4-(2-hydroxy-2-methylpropyl)-2-methylfuran-2-yl)-7a-methyl-1H-inden-4-ol (13a)

A solution of 13 (330 mg, 0.78 mmol) in dry THF (4 mL) was treated with ⁿBu₄NF (1.02 g, 3.25 mmol). The mixture was heated at reflux for 90 h. H₂O (20 mL) and EtOAc (20 mL) were added. The aqueous layer was extracted with EtOAc (4×20 mL) and the combined organic layer was dried (Na₂SO₄) and concentrated in vacuum. The residue was purified by flash chromatography (SiO₂, 2×5.5 cm, 30% EtOAc-hexanes) to give 13a (224 mg, 93%, white solid, mp: 98° C.).

Elementary Analysis Calculated for C₁₉H₃₄O₃: C, 73.50; H, 11.04; O, 15.46. Found C, 73.29, H, 11.35

(1S,3aR,7aR)-octahydro-1-((2S,4S)-tetrahydro-4-(2-hydroxy-2-methylpropyl)-2-methylfuran-2-yl)-7a-methylinden-4-one (1S)

A solution of 13a (123 mg, 0.4 mmol) in dry CH₂Cl₂ (10 mL) was treated with PDC (pyridinium dichromate, 0.6 g, 1.6 mmol). The mixture was stirred at room temperature for 20 h. The mixture was filtered and concentrated in vacuum. The residue was purified by flash chromatography (SiO₂, 3×5.5 cm, 20% EtOAc-hexanes) to give 1S (120 mg, 98%, white solid, mp: 87° C.). Elemental analysis C=73.80%, H=10.51%.

¹H-NMR (250 MHz, CDCl₃, δ, ppm): 0.65 (s, 3H, CH₃Cy), 1.13 (s, 6H, 2×CH₃—COH), 1.20 (s, 3H, CH₃—C—OCH₂), 3.29 (t, 1H, J=9.2 Hz CH₂OCy), 4.00 (t, 1H, J=7.8 Hz, OCH₂Cy)

¹³C-NMR (62.89 MHz, CDCl₃, δ, ppm): 13.42 (CH₃), 18.63 (CH₂), 22.41 (CH₂), 23.76 (CH₂), 27.81 (CH₃), 29.47 (CH₂), 29.99 (CH₃), 35.68 (CH), 38.93 (CH₂), 40.67 (CH₂) 46.59 (CH₂), 46.76 (CH₂), 49.90 (C) 59.68 (CH), 61.80 (CH), 70.45 (C), 73.08 (CH₂), 83.99 (C), 212.01 (C).

Elementary Analysis Calculated for C₁₉H₃₂O₃: C, 73.98; H, 10.46; O 15.56. Found C, 73.80, H, 10.51

(1S,3aR,7aR)-octahydro-1-((2S,4R)-tetrahydro-4-(2-hydroxy-2-methylpropyl)-2-methylfuran-2-yl)-7a-methylinden-4-one (1R)

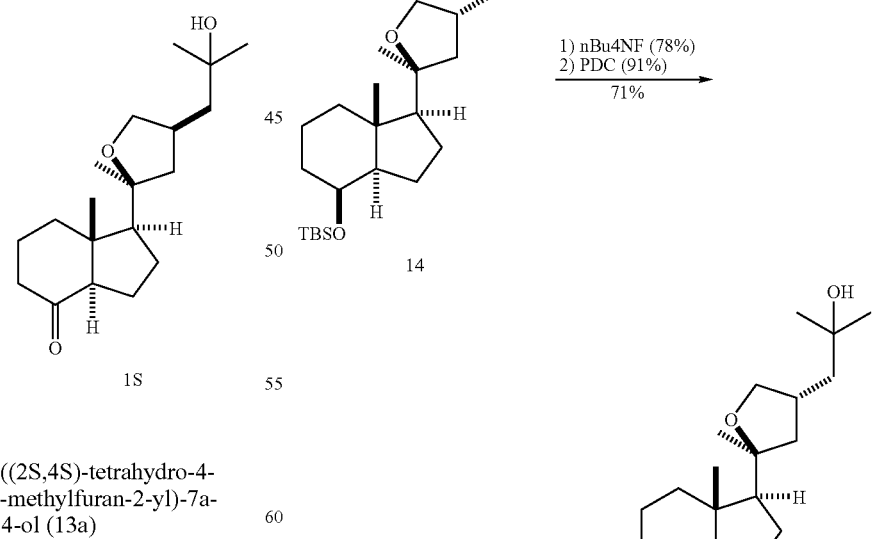

(1S,3aR,4S,7aS)-octahydro-1-((2S,4R)-tetrahydro-4-(2-hydroxy-2-methylpropyl)-2-methylfuran-2-yl)-7a-methyl-1H-inden-4-ol 14a A solution of 14 (280 mg, 0.78 mmol) in dry THF (4 mL) was treated with $^n$Bu$_4$NF (1.05 g, 3.3 mmol). The mixture was heated at reflux. After 115 h H$_2$O (20 mL) and EtOAc (20 mL) was added. The aqueous layer was extracted with EtOAc (4×20 mL) and the combined organic layer was dried (Na$_2$SO$_4$), filtered and concentrated in vacuum. The residue was purified by flash chromatography (SiO$_2$, 2×5.5 cm, 30% EtOAc-hexanes) to give the corresponding diol 14a (180 mg, 88%, white solid, mp: 67° C.).

(1S,3aR,7aR)-octahydro-1-((2S,4R)-tetrahydro-4-(2-hydroxy-2-methylpropyl)-2-methylfuran-2-yl)-7a-methylinden-4-one (1R)

A solution of 14a (100 mg, 0.32 mmol) in dry CH$_2$Cl$_2$ (10 mL) was treated with PDC (pyridinium dichromate, 0.5 g, 1.3 mmol). The mixture was stirred at room temperature for 20 h, the mixture was filtered and concentrated in vacuum. The residue was purified by flash chromatography (SiO$_2$, 3×5.5 cm, 20% EtOAc-hexanes) to give 1R (90 mg, 91%, white solid, mp: 82° C.).

$^1$H-NMR (250 MHz, CDCl$_3$, δ, ppm): 0.73 (s, 3H, CH$_3$Cy), 1.20 (s, 6H, 2×CH$_3$—COH), 1.22 (s, 3H, CH$_3$—C—OCH$_2$), 3.32 (dd, 1H, J=8.5 Hz, J=9.9 Hz, CH$_2$OCy), 4.09 (t, 1H, J=7.9 Hz, OCH$_2$Cy)

$^{13}$C-NMR (62.89 MHz, CDCl$_3$, δ, ppm): 14.12 (CH$_3$), 18.74 (CH$_2$), 22.52 (CH$_2$), 23.88 (CH$_2$), 27.58 (CH$_3$), 29.77 (CH$_3$), 30.04 (CH$_3$), 34.08 (CH), 39.07 (CH$_2$), 40.81 (CH$_2$) 45.73 (CH$_2$), 46.24 (CH$_2$), 49.89 (C) 59.64 (CH), 62.00 (CH), 70.72 (C), 75.06 (CH$_2$), 84.34 (C), 212.03 (C).

1-((3R,5S)-tetrahydro-5-((3S,3aS,7E,7aS)-octahydro-7-((Z)-2-((3S,5R)-3,5-Bis(triethylsilyloxy)-2-methylenecyclohexylidene)ethylidene)-3a-methyl-1H-inden-3-yl)-5-methylfuran-3-yl)-2-methylpropan-2-ol (16)

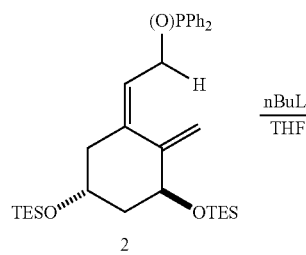

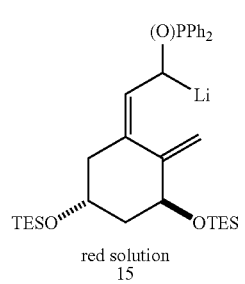

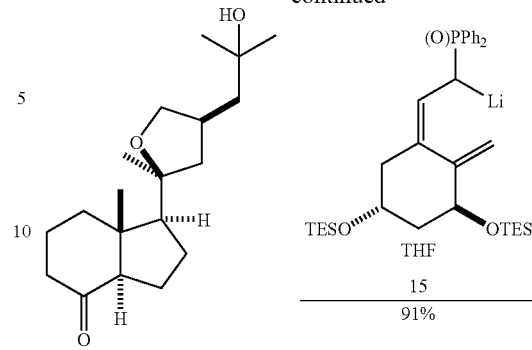

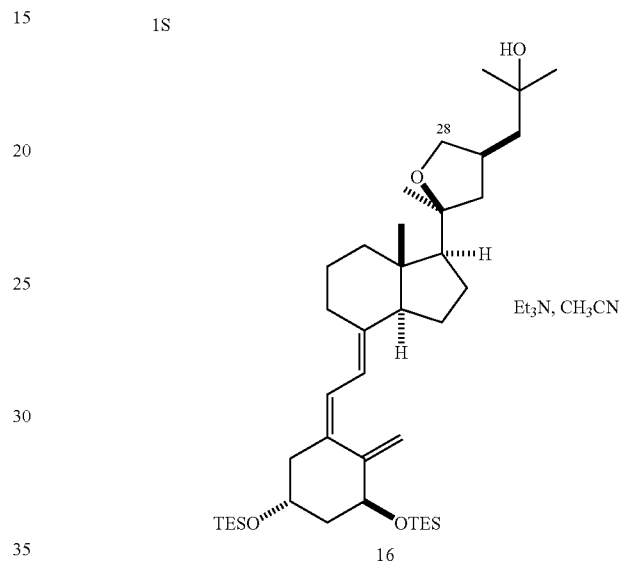

A solution of n-BuLi in hexane (0.74 mL, 1.68 mmol, 2.25 M) was added to a solution of phosphine oxide 2 (1.045 g, 1.8 mmol, 4.6 equiv) in dry THF at −78° C. The deep red solution was stirred for 1 h. A solution of ketone 1S (120 mg, 0.39 mmol, 1 equiv) in dry THF was added dropwise. The reaction mixture was stirred in the dark for 5 h at −78° C. and at −55° C. for 1 h. The reaction was quenched by the addition of H$_2$O (8 mL) and EtOAc (15 mL). Concentration of mixture gave a residue which was dissolved in Et$_2$O (100 mL). The combined layer was washed with saturated NaHCO$_3$ (3×25 mL), saturated NaCl (50 mL) and H$_2$O (50 mL), dried, filtered, and concentrated in vacuum. The residue was purified by flash chromatography (SiO$_2$, 3×15 cm, 40% Et$_2$O-hexanes) to give protected analogue 16 [150 mg, 91%, (Rf=0.7, 50% EtOAc/hexanes), colorless oil).

$^1$H-NMR (250 MHz, CDCl$_3$, δ, ppm): 0.5-0.6 (m, 15H, 6×CH$_3$—CH$_2$Si, CH$_3$-Cy), 0.92 (t, 18H, J=7.9 Hz, 6×CH$_3$CH$_2$—Si), 1.22 (s, 3H, CH$_3$—C—OCH$_2$), 1.17 (s, 6H, CH$_3$COH), 1.23 (s, 3H, CH$_3$—CO—CH$_2$), 3.34 (t, 1H, J=9.1 Hz, CH$_2$OCy), 4.03 (t, 1H, J=7.7 Hz, OCH$_2$Cy), 4.16 (m, 1H, HC—OH), 4.36 (t, 1H, J=4.9 Hz, H—COH of C$_1$), 4.8 (d, 1H, J=2 Hz, H$_2$C=), 5.19 (d, 1H, J=2 Hz, H—C=), 6.00 (d, 1H, J=11.2 Hz), 6.20 (d, 1H, J=11.2 Hz, H—C=).

$^{13}$C-NMR (62.89 MHz, CDCl$_3$, δ, ppm): 4.76 (CH$_2$), 4.79 (CH$_2$), 6.80 (CH$_3$), 6.85 (CH$_3$), 13.00 (CH$_3$), 21.73 (CH$_2$), 22.64 (CH$_2$), 23.30 (CH$_2$), 27.56 (CH$_3$), 28.78 (CH$_2$) 29.64 (CH$_3$), 30.08 (CH$_3$), 35.85 (CH) 40.76 (CH$_2$), 44.96 (CH$_2$), 45.92 (CH$_2$), 46.96 (CH$_2$), 47.05 (CH$_2$), 47.05 (C), 56.47 (CH), 59.92 (CH), 67.15 (CH), 70.83 (C), 71.35 (CH), 73.12

($CH_2$), 84.87 (C), 111.08 ($CH_2$), 118.16 (CH), 123.07 (CH), 135.04 (C), 140.61 (C), 148.30 (C).

1-((3S,5S)-tetrahydro-5-((3S,3aS,7E,7aS)-octahydro-7-((Z)-2-((3S,5R)-3,5-Bis(triethylsilyloxy)-2-methylenecyclohexylidene)ethylidene)-3a-methyl-1H-inden-3-yl)-5-methylfuran-3-yl)-2-methylpropan-2-ol (17)

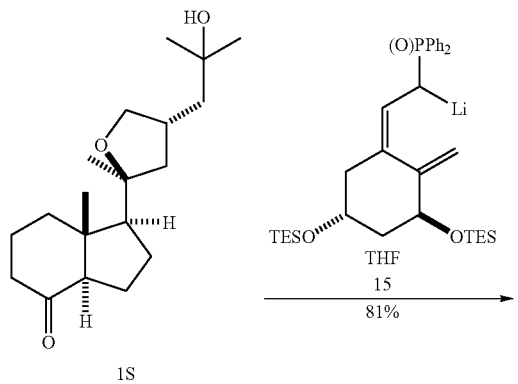

A solution of n-BuLi in hexanes (0.55 mL, 1.23 mmol, 2.25 M) was added to a solution of phosphine oxide 15 (785 mg, 1.3 mmol, 4.6 equiv) in dry THF at −78° C. The deep red solution was stirred for 1 h. A solution of ketone 1R (88 mg, 0.28 mmol, 1 equiv) in dry THF was added dropwise. The reaction mixture was stirred in the dark for 5 h at −78° C. and at −55° C. for 1 h. The reaction was quenched by the addition of $H_2O$ (8 mL) and EtOAc (15 mL). Concentration of mixture gave a residue which was dissolved in $Et_2O$ (100 mL). The combined layer was washed with saturated $NaHCO_3$ (3×25 mL), saturated NaCl (50 mL) and $H_2O$ (50 mL), dried, filtered, and concentrated in vacuum. The residue was purified by flash chromatography ($SiO_2$, 3×15 cm, 40% $Et_2O$-hexanes) to give protected analog 17 [120 mg, 81%, (Rf=0.7, 50% EtOAc/hexanes), colorless oil) and recovered 1R (20 mg).

$^1$H-NMR (250 MHz, $CDCl_3$, δ, ppm): 0.59 (q, J=7.8 Hz, 6H, $CH_3$—$CH_2$Si), 0.60 (q, J=7.5 Hz, 6H, $CH_3$—$CH_2$Si) 0.66 (s, 3H, $CH_3$-Cy), 0.94 (t, 18H, J=7.8 Hz, $CH_3CH_2$—Si), 1.21 (s, 6H, 2x$CH_3$—COH), 1.22 (s, 3H, $CH_3$—CO—$CH_2$), 3.34 (t, J=8.9 Hz, 1H, $CH_2$OCy), 4.10 (t, J=7.8 Hz, 1H, C$H_2$OCy), 4.18 (m, 1H, HC$^3$), 4.39 (t, 1H, J=4.9 Hz, HC$^3$), 4.88 (s, 1H, =$CH_2$), 5.21 (s, 1H, =$CH_2$), 6.03 (d, 1H, J=1.1 Hz, —HC=CH—), 6.23 (d, 1H, J=1.1 Hz, —HC=CH—).

$^{13}$C-NMR (62.89 MHz, $CDCl_3$, δ, ppm): 4.76 ($CH_2$), 4.79 ($CH_2$), 6.79 ($CH_3$), 6.84 ($CH_3$), 13.51 ($CH_3$), 21.75 ($CH_2$), 22.67 ($CH_2$), 23.32 ($CH_2$), 27.15 ($CH_3$), 28.76 ($CH_2$) 29.74 ($CH_3$), 30.02 ($CH_3$), 34.20 (CH) 40.75 ($CH_2$), 44.96 ($CH_2$), 45.81 ($CH_2$), 45.90 ($CH_2$), 46.02 ($CH_2$), 46.39 (C), 56.48 (CH), 59.86 (CH), 67.14 (CH), 70.79 (C), 71.37 (CH), 74.89 ($CH_2$), 85.06 (C), 111.10 ($CH_2$), 118.20 (CH), 123.07 (CH), 135.05 (C), 140.62 (C), 148.29 (C).

(1R,3S,5Z)-5-((E)-2-((1S,3aS,7aS)-hexahydro-1-((2S,4S)-tetrahydro-4-(2-hydroxy-2-methylpropyl)-2-methylfuran-2-yl)-7a-methyl-1H-inden-4(7aH)-ylidene)ethylidene)-4-methylenecyclohexane-1,3-diol (A)

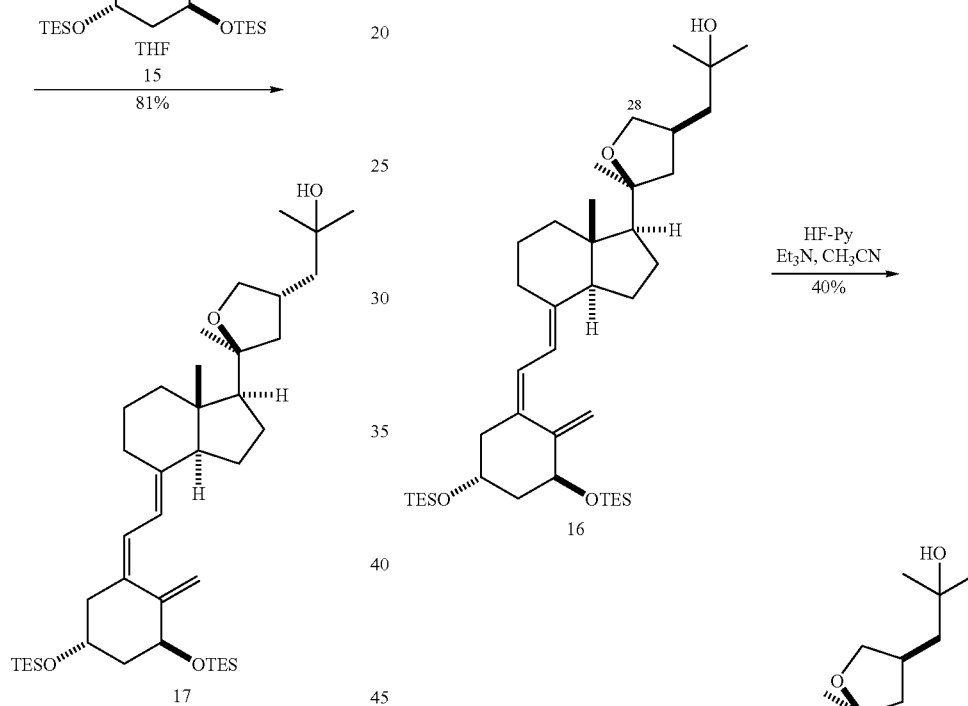

HF-Py (0.4 mL) was added to a solution of compound 16 (134 mg, 0.2 mmol) in $CH_3CN$ (2.5 mL) and $Et_3N$ (1.5 mL). After 10 min, the reaction was quenched by the addition of saturated $NaHCO_3$ (5 mL). The mixture was extracted with $Et_2O$ (2×20 mL). The combined organic phase was washed with saturated NaCl (25 mL) and $H_2O$ (25 mL), dried, filtered and concentrated in vacuum. The residue was purified by flash chromatography (SiO$_2$, 1.5×9.5 cm, 50% EtOAc-hexanes) to give compound A (80 mg, 88%, white solid, mp: 128° C.).

$^1$H-NMR (250 MHz, CDCl$_3$, δ, ppm): 0.62 (s, 3H, Cy-CH$_3$), 1.18 (s, 6H, 2×CH$_3$—C—OH), 1.23 (s, 3H, CH$_3$—C—O—CH$_2$—), 3.34 (t, 1H, J=9.1 Hz, C—O—CH$_2$), 4.03 (t, 1H, J=7.7 Hz, C—O—CH$_2$), 4.17 (m, 1H, HC—OH), 4.37 (m, 1H, HC—OH), 4.95 (s, 1H, H$_2$C=C), 5.29 (s, 1H, H$_2$C=C), 5.98 (d, 1H, J=11.1, =CH—HC=), 6.32 (d, 1H, J=11.1, =CH—HC=).

$^{13}$C-NMR (62.89 MHz, CDCl$_3$, δ, ppm): 13.12 (CH$_3$), 21.91 (CH$_2$), 22.62 (CH$_2$), 23.36 (CH$_2$), 27.58 (CH$_3$), 28.94 (CH$_2$) 29.63 (CH$_3$), 30.09 (CH$_3$), 35.82 (CH) 40.62 (CH$_2$), 42.76 (CH$_2$), 45.02 (CH$_2$), 46.05 (C), 46.82 (CH$_2$), 47.06 (CH$_2$), 56.44 (CH), 59.86 (CH), 66.68 (CH), 70.40 (C), 70.90 (CH), 73.08 (CH$_2$), 84.93 (C), 111.54 (CH$_2$), 117.38 (CH), 124.65 (CH), 133.24 (C), 142.49 (C), 147.66 (C).

(1R,3S,5Z)-5-((E)-2-((1S,3aS,7aS)-hexahydro-1-((2S,4R)-tetrahydro-4-(2-hydroxy-2-methylpropyl)-2-methylfuran-2-yl)-7a-methyl-1H-inden-4(7aH)-ylidene)ethylidene)-4-methylenecyclohexane-1,3-diol (B)

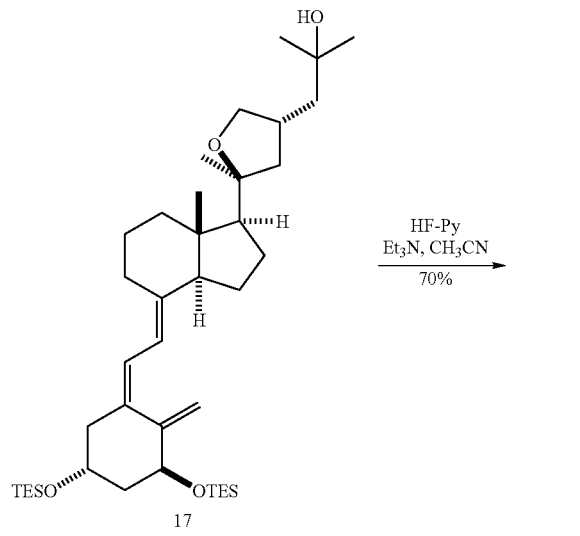

Compound B

HF-Py (0.4 mL) was added to a solution of compound 17 (117 mg, 0.17 mmol) in CH$_3$CN (2.5 mL) and Et$_3$N (1.5 mL). After 10 min, the reaction was quenched by the addition of saturated NaHCO$_3$ (5 mL). The mixture was extracted with Et$_2$O (2×20 mL). The combined organic phase was washed with saturated NaCl (25 mL) and H$_2$O (25 mL), dried, filtered and concentrated in vacuum. The residue was purified by flash chromatography (SiO$_2$, 1.5×11 cm, 50% EtOAc-hexanes) to give compound B (60 mg, 85%, white solid, mp: 96-C). 1H-NMR-13C-NMR. HRMS (FAB)

$^1$H-NMR (250 MHz, CDCl$_3$, δ, ppm): 0.67 (s, 3H, CH$_3$), 1.22 (s, 9H, 2×CH$_3$—C—OH, CH$_3$—C—O—CH$_2$—), 3.34 (dd, 1H, J=8.5, 9.7 Hz, C—O—CH$_2$), 4.11 (t, 1H, J=7.9 Hz, C—O—CH$_2$), 4.22 (m, 1H, HC—OH), 4.44 (m, 1H, HC—OH), 4.99 (s, 1H, H$_2$C=C), 5.32 (s, 1H, H$_2$C=C), 6.01 (d, 1H, J=11.3, =CH—HC=), 6.36 (d, 1H, J=11.3, =CH—HC=).

$^{13}$C-NMR (62.89 MHz, CDCl$_3$, δ, ppm): 13.64 (CH$_3$), 21.97 (CH$_2$), 22.64 (CH$_2$), 23.41 (CH$_2$), 27.26 (CH$_3$), 28.96 (CH$_2$) 29.78 (CH$_3$), 30.08 (CH$_3$), 34.22 (CH) 40.64 (CH$_2$), 42.79 (CH$_2$), 45.11 (CH$_2$), 46.00 (CH$_2$), 46.36 (CH$_2$), 46.36 (C), 56.50 (CH), 59.84 (CH), 66.80 (CH), 70.58 (C), 70.93 (CH), 74.97 (CH$_2$), 85.10 (C), 111.62 (CH$_2$), 117.38 (CH), 124.82 (CH), 133.08 (C), 142.72 (C), 147.65 (C).

II. In Vitro Assays

Materials and Methods
Purification and Crystallization

Crystals of the hVDR ligand binding domain (LBD) in complex with compounds A and B were obtained using the mutant lacking 50 residues in the loop connecting helix H1 and H3, used to solve the structure of the VDR LBD bound to 1α,25(OH)$_2$D$_3$ and several synthetic ligands (10-12). This mutant has the same biological properties (binding, transactivation in several cell lines, heterodimerization) as the VDR LBD wild type (11). Purification and crystallization of the human VDR LBD complexes with the new ligands were carried out by using the described procedure (11). The LBD of the human VDR (residues 118-427 Δ165-215) was cloned in pET28b expression vector to obtain an N-terminal hexa-histidine-tagged fusion protein and was overproduced in *E. Coli* BL21 (DE3). Cells were grown in LB medium and subsequently induced for 6 h at 20° C. with 1 mM isopropyl thio-β-D-galactoside. Protein purification included a metal affinity chromatography step on a cobalt-chelating resin. After tag removal by thrombin digestion, the protein was further purified by gel filtration. The final protein buffer was 10 mM Tris, pH7.5, 100 mM NaCl, and 5 mM dithiothreitol. The protein was concentrated to 10 mg/mL and incubated in the presence of a 5-fold excess of the ligands. The purity and homogeneity of the protein were assessed by SDS-PAGE and Native-PAGE. Crystals of the complexes were obtained at 4° C. by vapor diffusion in hanging drops. Crystals of VDR LBD-1α,25(OH)$_2$D$_3$ complex were used for micro-seeding; the seeds from serial dilutions introduced into freshly made drops. The reservoir solutions contained 100 mM Mes-KOH and 1.4 M ammonium sulphate at pH6.0.

X-Ray Data Collection and Structure Determination

The crystals were cryoprotected with a solution containing the reservoir solution plus 30% glycerol and 5% PEG400, mounted in fiber loops and flash cooled in liquid ethane at liquid N$_2$ temperature. Data collection from a single frozen crystal was performed at 100K at the beamline BM30 of the ESRF (Grenoble, France). The crystals were isomorphous and belonged to the orthorhombic space group P2$_1$2$_1$2, with the unit cells parameters as specified in Table 1. Data was integrated and scaled using the HKL2000 program package (13).

TABLE 1

Data Collection and Refinement statistics.

| Ligand | Compound A | Compound B |
|---|---|---|
| Wavelength | 0.9794 Å | 0.9796 Å |
| Space group | P2$_1$2$_1$2$_1$ | P2$_1$2$_1$2$_1$ |
| Cell dimensions | | |
| A | 45.01 Å | 45.06 Å |
| B | 51.37 Å | 51.46 Å |
| C | 132.24 Å | 132.13 Å |
| Resolution range (last shell) | 20-2.0 Å (2.07-2.0) | 20-1.8 Å (1.86-1.8) |
| Unique reflections | 21276 | 28589 |
| Completeness (last shell) | 99.7% (97.8%) | 99.5% (97.3%) |
| <I/δ(I)> | 30.2 (5.7) | 26.7 (4.2) |
| $^a$R-merge (last shell) | 0.062 (0.232) | 0.061 (0.294) |
| $^b$R$_{cryst}$ | 18.6% | 19.2% |
| $^c$R$_{free}$ | 21.7% | 20.6% |
| rmsd bond lengths | 0.005 Å | 0.005 Å |
| rmsd bond angles | 1.05° | 1.09° |
| Non-hydrogen protein atoms | 2019 | 2019 |
| Non-hydrogen ligand atoms | 32 | 32 |
| Solvent molecules | 159 | 193 |
| Average B factor for non-hydrogen atoms | | |
| Protein | 23.2 Å$^2$ | 18.3 Å$^2$ |
| Ligand | 14.3 Å$^2$ | 14.1 Å$^2$ |
| Solvent | 32.5 Å$^2$ | 28.1 Å$^2$ |

$^a$R-mereg: Σ|I$_h$ − <I$_h$>|/ΣI$_h$.
$^b$R$_{cryst}$: Σ|F$_o$ − F$_c$|/ΣF$_o$, where F$_o$ and F$_c$ are the observed and calculated structure factor amplitudes, respectively.
The $^c$R$_{free}$ value was calculated from 5% of all the data that were not used in the refinement.
Rmsd: root mean square deviation from ideal geometry.

The crystal structures of the VDR LBD complexes with compound A and compound B were solved by molecular replacement using the known human VDR LBD-1α,25(OH)$_2$D$_3$ structure as a starting model and refined at resolution 2.0 and 1.8 Å, respectively. The omit maps from the refined atomic model of VDR LBD were used to fit the ligands to their electron density. Anisotropic scaling and a bulk solvent correction, and restrained isotropic atomic B-factor refinement were used. The average temperature factors for the ligands (14.3 Å$^2$ and 14.1 Å$^2$ for compounds A and B, respectively) were lower than those for proteins (23.2 Å$^2$ and 18.3 Å$^2$ for compound A and compound B, respectively).

Alternate cycles of maximum likelihood refinement and model fitting were subsequently performed to generate the final models of the complexes. All data was included in the refinement (no δ-cutoffs). All refined models showed unambiguous chirality for the ligands and no Ramachandran plot outliers according to PROCHECK. The final models of VDR-A and VDR-B complexes contain 255 residues, with no clear electron density for the first two N-terminal residues and the last four C-terminal residues, and poor electron density for residues 375-377 in the loop connecting H9-H10. The crystallographic data is summarized in Table 1. The program MOLREP (14), CNS-SOLVE (15), and O (16) were used for molecular replacement, structure refinement, and model building. For the structure comparison, Cα traces of the models were superimposed using the lsq commands of O and default parameters. The figures were generated with Pymol (17).

Transfection and Transactivation Assay

The human VDR LBD was subcloned into the pG4M derived plasmid as a Gal fusion protein. Transient transfection experiments for the analysis of VDR activation were performed in 48 wells plates, using a standard calcium phosphate coprecipitation technique as described (11). 293 EBNA cells were seeded (6.0×10$^4$ cells per well) and incubated for 24 hours at 37° C. in medium containing Dulbecco medium (DMEM+1 g/L glucose), 10% FCS, gentamycine and 1 mg/ml G418 (geneticin). 293 EBNA cells were transiently transfected with 12.5 ng of Gal-4-VDR LBD plasmid, 10 ng of UAS-TATA-luciferase reporter plasmid, and 37.5 ng of PCH110 internal control recombinant expressing β-galactoside plasmid. After cells were incubated for 8 hours at 37° C., the medium was replaced and the compounds were added in optimized serial dilutions. After 20 hours at 37° C., cells were washed with PBS and harvested in Passiv lysis buffer (Promega). The cell lysates were assayed for lusiferase and β-galactosidase activity. Luciferase activity for each sample was normalized to β-galactosidase activity. Cells were treated with 1α, 25(OH)$_2$D$_3$, compound A, and compound B. All experiments were performed in duplicates.

Results and Discussion

Novel Side Chain Analogs

In the crystal structures of VDR complexed with several ligands (10-12), the ligand is tightly bound to the receptor around the A-, Seco B-, C- and D-rings. In contrast, the aliphatic side chain is less constrained, thus allowing alternative conformations of the side chain for the 1α,25(OH)$_2$D$_3$.

Two epimers, compound A and compound B, with opposite stereochemistry at C23 of an oxolane moiety were synthesized as described above (FIG. 1). Preliminary docking experiments showed that compound A and 1α,25(OH)$_2$D$_3$ could adopt a similar conformation, and that additional O21 and C28 atoms made new Van der Walls contacts with the Ligand Binding Pocket (LBP). On the other hand, compound B should adopt a different conformation and could induce a change of the protein structure. Experimental data were necessary to address both points.

The tests of their biological activity emphasized the expected differences. The results of transactivation in cellular transfection experiments are shown in FIG. 2.

At 10$^{-10}$ M, compound A induced transcriptional activities of human VDR 12 times more efficiently than 1α,25(OH)$_2$D$_3$. On the other hand, 1α,25(OH)$_2$D$_3$ and compound B induced transcriptional activities of human VDR with similar efficiency.

Ligand-Protein Interactions

The two complexes adopt the canonical conformation of all previously reported structures of VDR bound to agonist ligands. Variations concern only some side chains located at the surface of the protein. When compared with VDR-1α,25(OH)$_2$D$_3$ complex, the atomic models show r.m.s.d. on Cα atoms of 0.23 Å and 0.24 Å for VDR-A and VDR-B complexes respectively.

Compounds A and B adopt an elongated conformation, also observed in VDR-1α,25(OH)$_2$D$_3$ complex. For all three complexes, the distance between 1-OH and 25-OH varies from 12.8 Å to 13.1 Å. The interactions between the protein and the A-, Seco B-, C-, and D-rings are identical. The hydroxyl groups make the same hydrogen bonds, 1-OH with Ser-237 and Arg-274, 3-OH with Tyr-143 and Ser-278, and the 25-OH with His-305 and His-397.

In the crystal structure, the side chain of compound A adopts a conformation similar to that of 1α,25(OH)$_2$D$_3$ and thus forms all previously observed contacts contributing to the tighter ligand-protein contacts. A novel feature when compared to 1α,25(OH)$_2$D$_3$ is the additional van der Waals contact of O21 with Val-300, which is also present but weaker in the VDR-B complex. The stereoisomer B adopts a different side chain conformation due to the inverse configuration at C23. C23 and C24 are 0.6 Å and 1.2 Å away from their position in the compound A complex which affects the respective contacts. As a consequence, the positions of C25, C26, C27 and 25-OH are also different and the direct interaction of compound B with activation helix-12 is then weaker (C27-Val-418 of 4.6 Å).

Structure-Activity Relationship

The two crystal structures provide an explanation for the higher transactivation potency of one diastereomer (compound A). In the case of compound A, the oxolane ring stabilizes a conformation that mimics the bound form of the natural ligand. It adopts the energetically favorable half boat conformation which allows the side chain to fit without further tension as shown in the observed bond angle of C23-C24-C25 (118°), similar to that of 1α,25(OH)$_2$D$_3$ (121°). Further stability is also provided by the additional van der Waals contact of O21 with Val-300.

As for compound B, the additional van der Waals contacts with the LBP are compensated by the energetically unfavorable planar conformation of oxolane ring (torsion angles of O21-C20-C22-C23 and C20-C22-C23-C28 are −9° and −3°, respectively), larger C23-C24-C25 bond ample (124°), and the weaker interaction of C27 with Val-418.

The new ring fulfills two functions: (i) a larger fraction of the LBP is occupied by the ligand thus giving rise to additional stabilizing contacts, and (ii) the active form of the bound ligand is favored by the ring pucker. This last characteristic is equivalent to a discrimination factor that restrains the ligand's conformation ensemble to a smaller number of samples making the binding process more efficient (6). Stabilization of a bound conformation energetically favorable is equivalent to the selection of an optimal conformer within an ensemble and has clear entropic advantages for an induced fit process (18). This should affect the ligand specificity as well as the binding kinetic.

The present analysis suggests a possibility for further improvement of the potency and the specificity of the ligand. An easy way to increase the stability of the complex is to fill up more of the ligand binding pocket and increasing thereby the number of contacts between protein and ligand. A methylation at position C2, for instance, would meet the requirement since the crystal structure of VDR in complex with 1α,25(OH)$_2$D$_3$ shows an empty cavity at this location. Indeed a methyl group on C2α compound has been synthesized and exhibits a higher binding affinity (19). The methylation at position C2α of compounds A and B should increase the superagonist character of the ligands.

III. In Vivo Experiments

Male C57BL/6J mice, 6-7 weeks of age, were obtained from Charles River Laboratories France (l'Arbresle, France). All mice were maintained in a temperature-controlled (23° C.) facility with a 12 h light/dark cycle and were given free access to food and water. The mice were fed the EQ12310 diet from UAR (Villemoison sur Orge, France), which contained 16.8% protein, 73.5% carbohydrate and 4.8% fat. The different VDR agonists were dissolved in sesame oil and administered by oral gavage at the indicated doses. The mice were fasted 4 h before harvesting blood for subsequent Calcium measurements, which were performed as described (1).

In an initial experiment 12 male C57BL/6J mice were gavaged for 7 days with either 2 μg/kg of 1α,25(OH)$_2$D$_3$, 2 μg/kg of compound A, and 2 μg/kg of compound B. At this dose all compounds induced an increase in serum calcium levels which was more pronounced for 1α,25(OH)$_2$D$_3$ and compound A (FIG. 3.1). Thereafter a detailed dose response (0.2, 0.5, 1, and 2 μg/kg) was performed with both 1α,25(OH)$_2$D$_3$, and compound A (FIG. 3.2). In this study compounds were gavaged during 4 consecutive days. Interestingly and consistent with the transfection studies, compound A had a weaker effect on serum calcium levels, which only became significant at the dose of 2 μg/kg, then that of 1α,25(OH)$_2$D$_3$, which was already causing hypercalcemia at the dose of 1 μg/kg.

These new compounds are promising VDR agonists with significantly lower calcemic activities in vivo.

REFERENCES

1) Laudet, V., & Gronemeyer H. (2002) The Nuclear Receptor Facts Book, Academic Press, London.
2) Glass, C. K., & Rosenfeld, M. G. (2000) *Genes Dev.* 14, 121-141.
3) Greschik, H., & Moras, D. (2003) *Curr. Top. Med. Chem.* 3, 1573-1599.
4). Smith, C. L., & O'Malley, B. W. (2004) *Endocr. Rev.* 25, 45-71.
5) Bouillon, R., Verstuyf, A., Verlinden, L., Eelen, G., & Mathieu, C. (2003) *Recent Results Cancer Res.* 164, 353-356.
6) Norman, A. W., Mizwicki, M. T., & Norman, D. P. (2004) *Nat. Rev. Drug Discov.* 3, 27-41.
7) DeLuca HF (2004) *Am. J. Clin. Nutr.* 80, 1689S-1696S.
8) Peleg, S., S Sastry, M., Collins, E. D., Bishop, J. E. & Norman, A. W. (1995) *J. Biol. Chem.* 270, 10551-10558.
9) Yamamoto, H., Shevde, N. K., Warrier, A., Plum, L. A., DeLuca, H. F., & Pike, J. W. (2003) *J. Biol. Chem.* 278, 31756-31765.
10) Eelen, G., Verlinden, L., Rochel, N., Claessens, F., De Clercq, P., Vandewalle, M., Tocchini-Valentini, G., Moras, D., Bouillon, R., & Verstuyf, A. (2005) *Mol. Pharmacol.* 67, 1566-1573.
11) Rochel, N., Wurtz, J. M., Mitschler, A., Klaholz, B., & Moras, D. (2000) *Mol Cell* 5, 173-179.
12) Tocchini-Valentini, G., Rochel, N., Wurtz, J. M., Mitschler, A., & Moras, D. (2001) *Proc Natl Acad Sci USA* 98, 5491-5496.
13) Otwinowski Z., & Minor, W. (1997) *Methods Enzymol.* 276, 307-326.
14) Vagin, A., & Teplyakov, A. (1997) *J. Appl. Crystallogr.* 30, 1022-1025.
15) Brunger, A. W., Jiang, J. S., Kuszewski, J., Nilges, M., Pannu, N. S., et al. (1998) *Acta Crystallogr. D.* 54, 905-921.
16) Jones, T. A., Zou, J. Y., Cowan, S. W. & Kjeldgaard. (1991) *Acta Crystallogr. A* 47, 110-119.
17) DeLano, W. L. The PyMOL Molecular Graphics System (2002) DeLano Scientific, San Carlos, Calif., USA.
18) Billas, I. M., Twema, T., Garnier, J. M., Mitschler, A., Rochel, N., & Moras, D. (2003). *Nature* 426, 91-96.
19) Konno, K, Fujishima T, Maki S, Liu Z, Miura D, Chokki M, Ishizuka S, Yamaguchi K, Kan Y, Kurihara M, Miyata N, Smith C, DeLuca HF, & Takayama H. (2000). *J. Med. Chem.* 43, 4247-4265.

The invention claimed is:

1. A compound presenting the following formula (I):

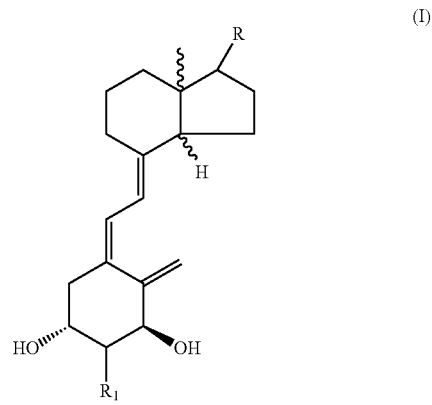

wherein R$_1$ represents a group selected from a hydrogen atom, a halogen atom, a linear or branched (C$_1$-C$_{10}$) alkyl, an (C$_1$-C$_{10}$)alkoxy, C$_2$-C$_{10}$ branched or linear alkenyl or C$_2$-C$_{10}$ branched or linear alkynyl, an (C$_5$-C$_{14}$)

aryl, and an (C$_5$-C$_{14}$)aryloxy group, in which said group is optionally substituted by at least one halogen atom, hydroxyl or —NH$_2$ group;
and wherein R represents

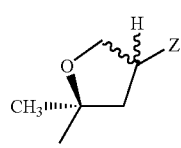
(II)

in which Z represents

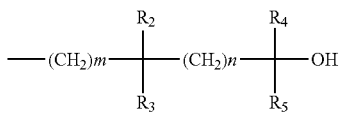
(III)

wherein:
R$_2$ and R$_3$, identical or different, represent a group selected from H, halogen atom, a C$_1$-C$_{10}$ branched or linear alkyl, C$_2$-C$_{10}$ branched or linear alkenyl or C$_2$-C$_{10}$ branched or linear alkynyl group;
R$_4$ and R$_5$, identical or different, represent a group selected from H, halogen atom, a C$_1$-C$_6$ linear or branched alkyl, C$_2$-C$_{10}$ branched or linear alkenyl or C$_2$-C$_{10}$ branched or linear alkynyl group;
m represents an integer comprised between 0 and 5; and
n represents an integer comprised between 0 and 5.

2. The compound according to claim 1, wherein R$_1$ represents a group selected from H, halogen atom, CH$_3$, (CH$_2$)$_3$OH or O(CH$_2$)$_3$OH.

3. The compound according to claim 1, wherein R represents:

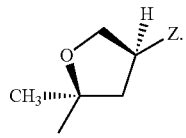

4. The compound according to claim 1, wherein m is 0 or 1.
5. The compound according to claims 1, wherein n is 0.
6. The compound according to claim 1, wherein R$_2$ and R$_3$, identical or different, represent a group selected from H, halogen atom and a C$_1$-C$_4$ branched or linear alkyl.

7. The compound according to claim 1, wherein R$_4$ and R$_5$, identical or different, represent a group selected from H, halogen atom and a C$_1$-C$_4$ linear or branched alkyl.

8. The compound according to claim 1, wherein said compound is the specific stereoisomer according to the following formula (IV):

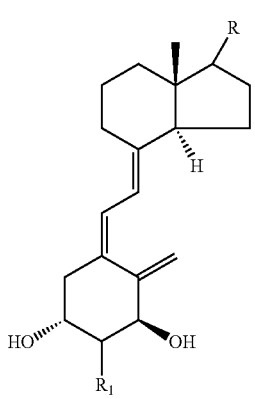
(IV)

wherein R$_1$ and R are as defined in claim 1.

9. The compound according to claim 8, wherein R represents

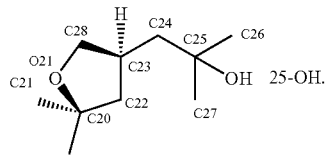

10. The compound according to claim 8, wherein R represents

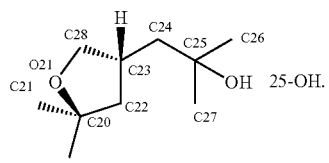

11. A pharmaceutical composition comprising at least one compound according to claim 1 and a pharmaceutically acceptable support, optionally with another active agent.

* * * * *